United States Patent [19]
Hunter et al.

[11] Patent Number: 5,811,088
[45] Date of Patent: Sep. 22, 1998

[54] ANTIINFECTIVE COMPOUNDS AND METHODS OF USE

[75] Inventors: Robert L. Hunter, Tucker; R. Martin Emanuele; Hameedsulthan S. Allaudeen, both of Alpharetta, all of Ga.

[73] Assignee: Emory University, Atlanta, Ga.

[21] Appl. No.: 457,808

[22] Filed: Jun. 1, 1995

Related U.S. Application Data

[63] Continuation of Ser. No. 161,551, Dec. 2, 1993, abandoned, which is a continuation-in-part of Ser. No. 81,006, Jun. 22, 1993, abandoned, which is a continuation of Ser. No. 760,808, Sep. 16, 1991, abandoned, which is a continuation of Ser. No. 419,016, Oct. 10, 1989, abandoned, which is a continuation-in-part of Ser. No. 150,731, Feb. 16, 1988, abandoned, which is a continuation-in-part of Ser. No. 141,668, Jan. 7, 1988, abandoned, which is a continuation of Ser. No. 17,330, Feb. 20, 1987, abandoned.

[51] Int. Cl.$^6$ .......................... A61K 31/74; A61K 31/765
[52] U.S. Cl. ...................................... 424/78.08; 424/78.17
[58] Field of Search ............................... 424/78.08, 78.17

[56] References Cited

U.S. PATENT DOCUMENTS

| | | |
|---|---|---|
| Re. 29,909 | 2/1979 | Kurtz . |
| 2,674,619 | 4/1954 | Lundsted . |
| 2,854,378 | 9/1958 | Buckwalter . |
| 2,979,528 | 4/1961 | Lundsted . |
| 3,022,335 | 2/1962 | Lundsted . |
| 3,036,118 | 5/1962 | Jackson et al. . |
| 3,089,818 | 5/1963 | Stone . |
| 3,140,232 | 7/1964 | Noseworthy . |
| 3,228,834 | 1/1966 | Gans et al. . |
| 3,450,502 | 6/1969 | Hymes . |
| 3,577,522 | 5/1971 | Hymes . |
| 3,590,125 | 6/1971 | Hymes . |
| 3,641,240 | 2/1972 | Hymes et al. . |
| 3,740,421 | 6/1973 | Schmolka . |
| 3,867,521 | 2/1975 | Miskel et al. . |
| 3,867,533 | 2/1975 | Schmolka . |
| 4,100,271 | 7/1978 | Krezanoski . |
| 4,323,560 | 4/1982 | Baschang et al. . |
| 4,395,393 | 7/1983 | Schmolka . |
| 4,407,790 | 10/1983 | Oakes et al. . |
| 4,409,209 | 10/1983 | Baschang et al. . |
| 4,410,660 | 10/1983 | Straus . |
| 4,423,038 | 12/1983 | Baschang et al. . |
| 4,489,158 | 12/1984 | Straus . |
| 4,575,484 | 3/1986 | Straus . |
| 4,606,918 | 8/1986 | Allison et al. . |
| 4,609,546 | 9/1986 | Hiratani . |
| 4,801,452 | 1/1989 | Hunter et al. . |
| 4,837,014 | 6/1989 | Hunter et al. . |
| 4,837,083 | 6/1989 | Hunter et al. . |
| 4,879,109 | 11/1989 | Hunter . |
| 4,897,263 | 1/1990 | Hunter . |
| 4,937,070 | 6/1990 | Hunter . |
| 4,997,644 | 3/1991 | Hunter . |
| 5,017,370 | 5/1991 | Hunter et al. . |
| 5,028,599 | 7/1991 | Hunter . |
| 5,030,448 | 7/1991 | Hunter . |
| 5,032,394 | 7/1991 | Hunter . |
| 5,039,520 | 8/1991 | Hunter . |
| 5,041,288 | 8/1991 | Hunter . |
| 5,047,236 | 9/1991 | Hunter et al. . |
| 5,064,643 | 11/1991 | Hunter et al. . |
| 5,071,649 | 12/1991 | Hunter . |
| 5,078,995 | 1/1992 | Hunter et al. . |
| 5,080,894 | 1/1992 | Hunter et al. . |
| 5,089,260 | 2/1992 | Hunter et al. . |
| 5,250,294 | 10/1993 | Hunter et al. . |

FOREIGN PATENT DOCUMENTS

| | | |
|---|---|---|
| 1106277 | 8/1981 | Canada . |
| 0 000 704 | 7/1978 | European Pat. Off. . |
| 0003999 | 2/1979 | European Pat. Off. . |
| 0011237 | 5/1980 | European Pat. Off. . |
| 0 049 422 | 9/1981 | European Pat. Off. . |
| 0 103 290 | 9/1983 | European Pat. Off. . |
| 2081436 | 1/1971 | France . |
| 2708152 | 2/1977 | Germany . |
| 87/06831 | 11/1987 | WIPO . |
| 87/06836 | 11/1987 | WIPO . |

OTHER PUBLICATIONS

Cornforth et al., "Antituberculosis Effect of Certain Surface–Active Polyoxyethylene Ethers in Mice," *Nature*, vol. 168, pp. 150–153 (1951).

Lin, T. S. and Prusoff, W. H., "Synthesis and Biological Activity of Several Amio Analogs of Thymidine," *J. Med. Chem.*, vol. 21, pp. 109–112 (1978).

McDougal, J. S., et al., "Immunoassay for the detection and Quantitation of infectious human retrovirus, lymphadenopathy–associated virus (LAV)," *J. Immun. Meth.* vol. 76, pp. 171–183 (1985).

Groopman, J. E., et al., "Characterization of serum neutralization response to the human immunodeficiency virus (HIV)," *AIDS Res. Human Retro.*, vol. 3, pp. 71–85 (1987).

Spira, et al. "Micromethod for assaying the reverse transcriptase of LAV–HTLV–III/lymphadenopathy–associated virus." *J. Clin. Microbiol.*, vol. 25, pp. 97–99 (1987).

(List continued on next page.)

Primary Examiner—Shean C. Wu
Attorney, Agent, or Firm—Jones & Askew

[57] ABSTRACT

In accordance with the present invention, a composition and method is provided that is effective in treating infections caused by microorganisms including, but not limited to, bacteria, viruses, and fungi. The present invention is effective in inhibiting the growth of bacteria such as Mycobacterium species including, but not limited to, *Mycobacterium avium-intracellulare* complex and *M. tuberculosis*. The present invention comprises a surface active copolymer, preferably an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 1200 to 15,000, and b is an integer such that the hydrophile portion represented by $(C_2H_4O)$ constitutes approximately 1% to 50% by weight of the compound.

86 Claims, 19 Drawing Sheets

OTHER PUBLICATIONS

Schinazi, R.F. et al., "Combinations of Isoprinosine and 3'–Azido–3'–Deoxythymidine in Lymphocytes Infected with Human Immunodeficiency Virus Type 1," *Antimicrob. Agents Chemother.* vol. 32, pp. 1784–1789 (1988).

Schinazi, R.F. et al., "Effect of combination of acyclovir, and vidarabine or its 5'–monophosphate on herpes simplex viruses in cell culture and in mice," *Antimicrob. Agents Chemother.*, vol. 22, pp. 499–507 (1982).

Chou, T. C., and Talalay, P. "Quantitatuve analysis of dose–effect relationships: the combined effects of multiple drugs or enzyme inhibitors," *Adv. Enz. Regul.*, vol. 22, pp. 27–55 (1984).

Weintraub, Harold M., "Antisense RNA and DNA," *Scientific American*, pp. 40–46 (Jan. 1990).

Atkinson, T.P. et al., "Ion transport mediated by copolymers composed of polyoxyethylene and polyoxypropylene," pp. C20–C26 (1988).

Benner, K.U. et al., "Uber die Wirkung von Pluronic® F68, einem Poloxypropylen–Polyoxyyyathylen–Kondensat, auf die ADP–induzierte Thrombocytenaggregation in vitro (The Effect of Pluronic® F68, a Polyoxypropylenepolyoxyethylene Condensate, on ADP–induced Platelet Aggregation in Vitro)," *Pfugers Arch.*, vol. 315, pp. 45–52 (1970).

Benner, K.U., et al., "Cold–Induced Platelet Aggregation In Vivo And Its Inhibition By A Nonionic Surface Active Substance," *Thrombosis Research*, vol. 2, pp. 331–342 (1973).

Block, N.L. et al., "Acutely Traumatized Canine Ureter. Effects of Low Molecular Weight Dextran and Surfactant Pluronic F–68," *Urology*, vol. 3, No. 2, pp.190–194 (Feb. 1974).

Byars, N.E. et al., "Adjuvant formulation for use in vaccines to elicit both cell–mediated and humoral immunity," *Vaccine*, vol. 5, pp. 223–228 (Sep. 1987).

Gaehtgens, P., et al., "Disaggregation of Human Red Blood Cells by Various Surface–Active Agents as Related to Changes of Cell Shape and Hemolysis", *Act Heamat.* vol. 53, pp. 82–89 (1975).

Grover, F.L., et al., "A Nonionic Surfactant And Blood Viscosity," *Arch. Surg.*, vol. 106, pp. 307–310 (1973).

Grover, F.L., et al, "The Effect of Pluronic® F–68 On Circulatory Dynamics And Renal And Carotid Artery Flow During Hemorrhagic Shock," *Journal of Surgical Research*, vol. 17, pp. 30–35 (1974).

Hoie, J., et al., "Effects of Pluronic® F68, Poloralkol, On Vascular Resistance In Vivo," *Journal of Surgical Research*, vol. 11, pp. 515–517 (1971).

Hunter, R.L. et al., "Nonionic Block Coploymer Surfactants as Immunological Adjuvants: Mecanisms of Action and Novel Formulations," *Immunological Adjuvants and Vaccines*, ed. by Gregoriadis, G. et al., Plenum Publishing Corp., pp. 133–144 (1989).

Hunter, R.L. et al., "The Adjuvant Activity of Nonionic Block Polymer Surfactants. III. Characterization of Selected Biologically Active Surfaces," *Scand. J. Immunol.*, vol. 23, pp. 287–300 (1986).

Hunter R. L. et al., "Adjuvant activity of non–ionic block copolymers. IV. Effect of molecular weight and formulation on titre and isotype of antibody," *Vaccine*, vol. 9, pp.250–256 (Apr. 1991).

Hymes, A.C., et al., "The Influence Of An Industrial Surfactant Pluronic® F–68, In The Treatment of Hemorrhagic Shock," *Journal of Surgical Research*, vol. 11, pp. 191–197 (1971).

Ketchum, L.D., et al. "Experimental Use Of Pluronic® F–68 In Microvascular Surgery," *Plastic and Reconstructive Surgery*, vol. 53, pp. 288–292 (1974).

Ketchum, L.D., "Pharmacological alterations in the clotting mechansim: Use in microvascular surgery," *Journal of Hand Surgery*, vol. 3, pp. 407–415 (1978).

Knize, D.M., et al., "Use of Antisludging Agents in Experimental Cold Injuries," *Surgery, Gynecology & Obstetrics*, vol. 129, pp. 1019–1026 (1969).

Lane, T.A., et al., "Reduction in the toxicity of a component of an artificial blood substitute by supercritical fluid fractionation," *Transfusion*, vol. 28, pp. 375–378 (1987).

Moore, A.R., et al, "Reduction Of Splenic Vascular Resistance During Profusion By Pluronic® F–68," *Journal of Surgical Research*, vol. 8, pp. 563–566 (1968).

Paton, B.C. et al. "The use of a nonionic detergent added to organ perfusates," *Organ Perfusion and Preservation*, ed. by Norman, J.C., Appleton–Century–Crofts, pp. 105–120 (1968).

Schmolka, I.R. et al., "Artificial Skin I. Preparation and Properties of Pluronic F–127 Gels for Treatment of Burns," *J. Biomed. Mater. Res.*, vol. 6, pp. 571–582 (1972).

Snippe, H. et al., "Adjuvant Effect of Nonionic Block Polymer Surfactants in Humoral and Cellular Immunity," *Int. Archs Allergy appl. Immun.*, vol. 65, pp. 390–398 (1981).

Takayama, K. et al., "Adjuvant activity of non–ionic block copolymers. V. Modulation of antibody isotype by lipopolysaccharides, lipid A and precursors," *Vaccine*, vol. 9, pp. 257–265 (Apr. 1991).

Vasko, K. A., et al., "Poloxalkol® (Pluronic F–68): A Priming Solution of Cardiopulmonary Bypass," *Trans. Am. Soc. Artif. Int. Organs*, 18, 526–531 (1972).

Williams, J.H. et al., "Modulation of Rat Granulocyte Traffic by a Surface Active Agent in Vitro and Bleomycin Injury," *Proceedings of the Society for Experimental Biology and Medicine*, vol. 188, pp. 461–470 (1988).

Matsukura, M. et al., "Phosphorothioate analogs of oligodeoxynucleotides:Inhibitors of replication and cytopathic effects of human immunodeficiency virus," *Proc. Natl. Acad. Sci.*, vol. 84, pp. 7706–7710 (Nov. 1987).

Cornforth et al., Chem. Abstracts, 46 #2696 (1952).

Rodeheavier et al, "Pluronic F–68: A Promising New Skin Wound Cleanser," *Ann. Emerg. Med.*, vol. 9, No. 11, pp. 572–576 (1980).

Rodeheavier et al, "Mechanical Cleansing of Contaminated Wounds with Surfactant," *Am. J. Surg.*, vol. 129, No. 3, pp. 241–245 (1975).

Hunter et al, "The Adjuvant Activity of Nonionic Block Copolymer Surfactants," J. of Immunology, vol. 127, No. 3, pp. 1244–1250 (1981).

Ceresa, R.J., "The Applications of Block Copolymer Polyol Surfactants," *Block & Graft Copolymerization*, vol. 2, pp. 174–272 (1976).

Schmolka, I., "A Review of Block Polymer Surfactants," *J. Am. Oil. Chem. Soc.*, vol. 54, No. 3, pp. 110–116 (1977).

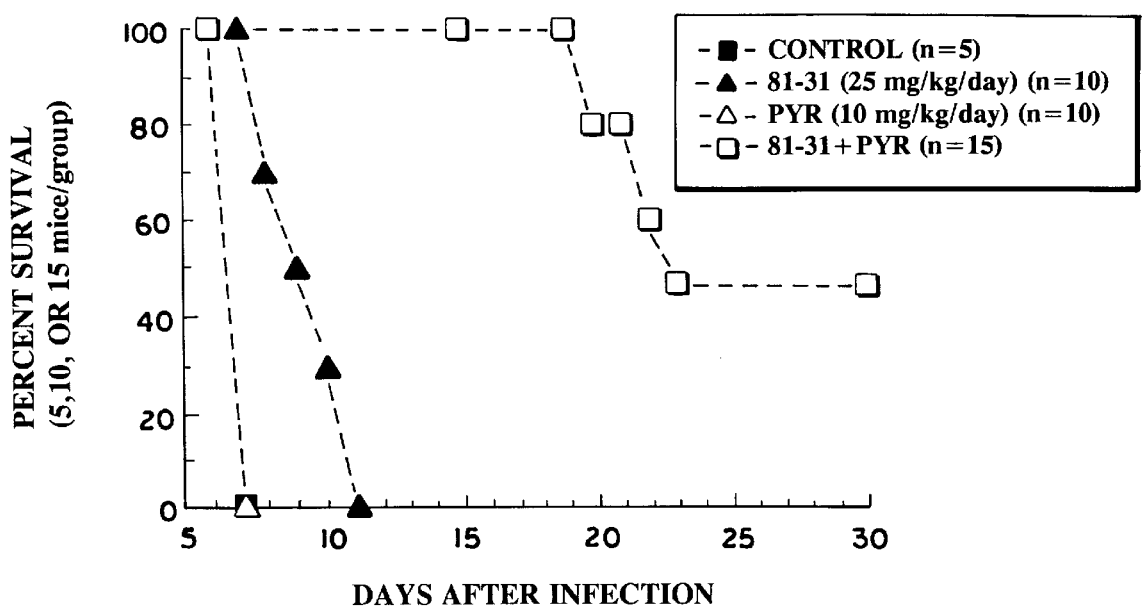
Fig_14
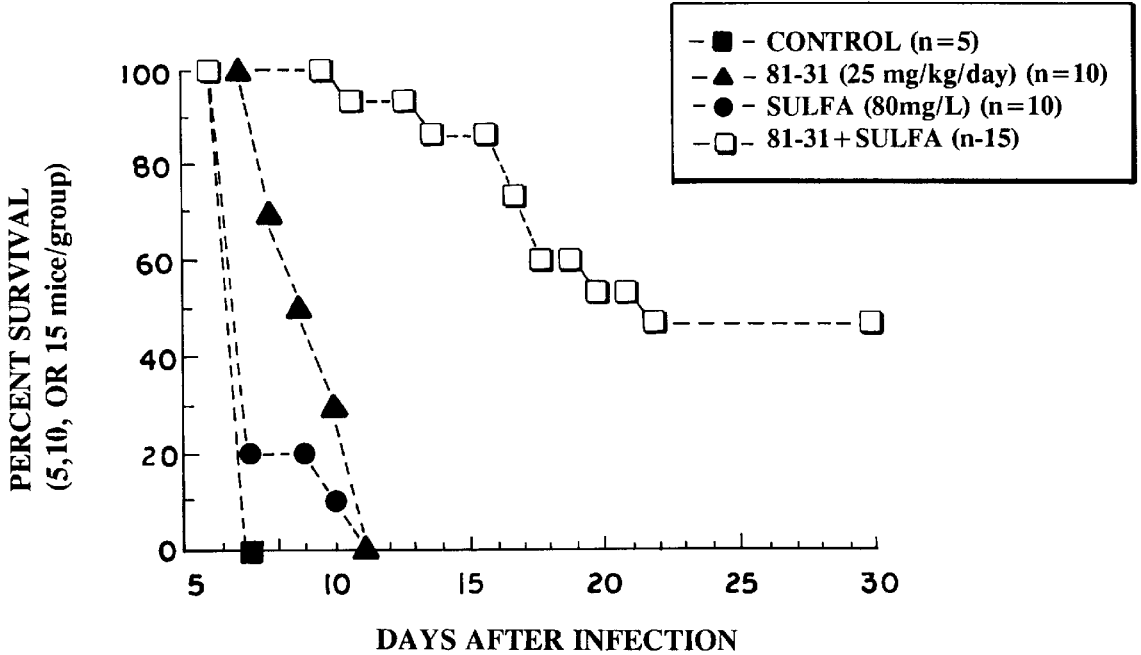
Fig_15

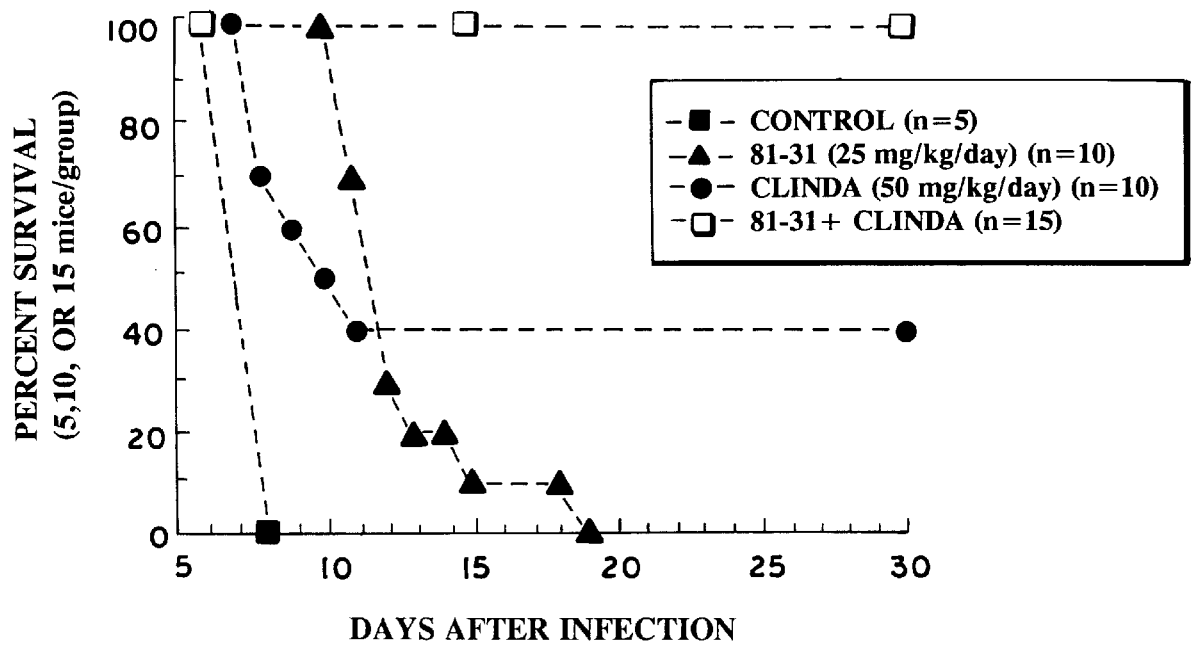
Fig_16
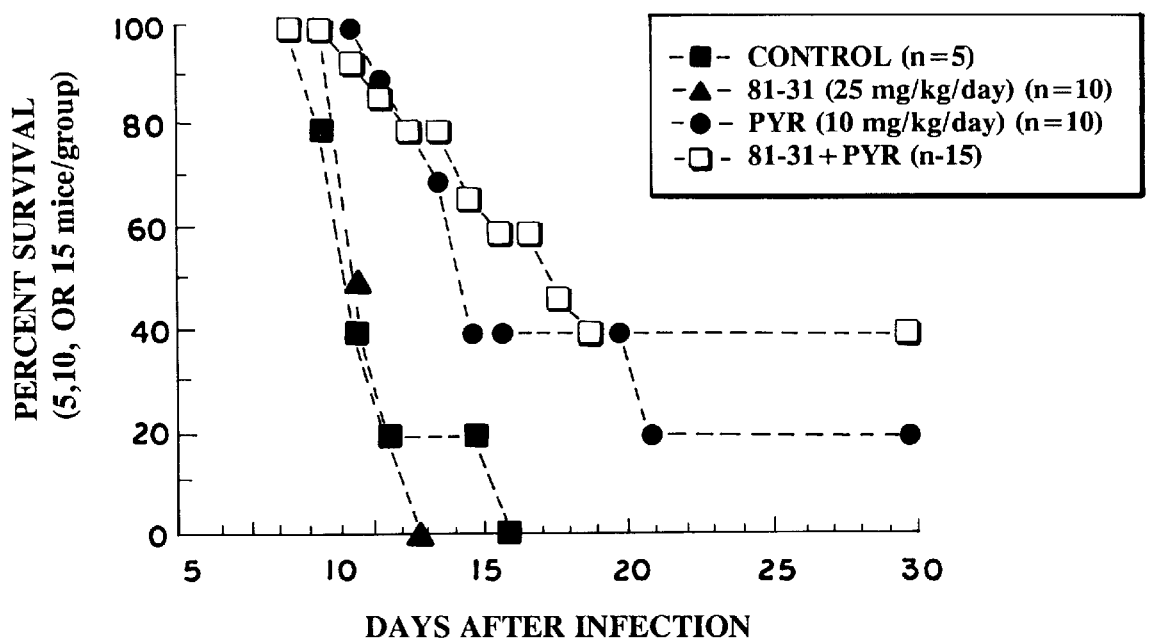
Fig_17

ANTIINFECTIVE COMPOUNDS AND METHODS OF USE

CROSS-REFERENCE TO RELATED APPLICATIONS

This is a continuation of application Ser. No. 08/161,551, filed Dec. 2, 1993, now abandoned which is a continuation-in-part of U.S. patent application Ser. No. 08/081,006, filed Jun. 22, 1993, now abandoned, which is a continuation of U.S. patent application Ser. No. 07/760,808 filed Sep. 16, 1991, now abandoned, which is a continuation of U.S. patent application Ser. No. 07/419,016 filed Oct. 10, 1989, now abandoned, which is a continuation-in-part application of U.S. patent application Ser. No. 07/150,731 filed on Feb. 16, 1988, now abandoned, which is a continuation-in-part of U.S. patent application Ser. No. 07/141,668 filed on Jan. 7, 1988, now abandoned, which is a continuation of U.S. patent application Ser. No. 07/017,330, filed on Feb. 20, 1987, now abandoned.

TECHNICAL FIELD

The present invention relates to antiinfective compounds and more particularly to compounds and methods that kill or suppress the growth of bacteria, viruses, fungi and protozoa. The compounds and methods are effective in controlling intracellular organisms.

BACKGROUND OF THE INVENTION

Tuberculosis has been a major killing disease of mankind for most of recorded history. The incidence of the disease declined in parallel with advancing standards of living since at least the mid-nineteenth century. However, in spite of the efforts of numerous health organizations worldwide, the eradication of tuberculosis (TB) has never been achieved, nor is it imminent. Nearly half of the world's population is infected with *M. tuberculosis,* with approximately 8 million new cases and there million deaths attributable to TB yearly.

After decades of decline, TB is on the rise, even in the United States where up to 10 million individuals are believed to be infected. Almost 28,000 new cases were reported in 1990, a 9.4 percent increase over 1989. A sixteen percent increase was observed from 1985 to 1990. TB is acquired by the respiratory route; actively infected individuals spread this infection efficiently by coughing or sneezing "droplet nuclei" which contain viable bacilli. Overcrowded living conditions and shared air spaces are especially conducive to the spread of TB, underlying the increase in instances that have been observed in the U.S. in prison inmates and among the homeless in larger cities.

Alarmingly, outbreaks of TB cases resistant to at least two of the most effective anti-TB drugs (rifampin [RFP] and isoniazide [INH]) are being reported in hospitals and correctional facilities with evidence of transmission to human immunodeficiency virus (HIV) negative individuals. Approximately half the patients with acquired immune deficiency syndrome (AIDS) will acquire a mycobacterial infection, with TB being an especially devastating complication. AIDS patients are at higher risks of developing clinical TB and anti-TB treatment seems to be less effective. Consequently, the infection often progresses to a fatal disseminated disease.

Presently an extremely disturbing phenomenon is the emergence of drug resistant *M. tuberculosis.* The rate of new TB cases proven resistant to at least one standard drug increased from 10 percent in the early 1980's to 23 percent in 1991. Currently, seven percent of all cases of TB are resistant to at least one drug, over double the number from the early 1980.

Additionally, mycobacteria other than *M. tuberculosis* are also becoming increasingly problematic as elements in the list of opportunistic infections that plague the AIDS patient. Organisms from the Avium-intracellulare complex (MAC), especially sero types four and eight, account for 68% of the mycobacterial isolates from AIDS patients. Enormous numbers of MAC are found (up to $10^{10}$ acid-fast bacilli per gram of tissue) and, consequently the prognosis for the infected AIDS patient is poor.

Mycobacteria, including *Mycobacterium avium,* are intracellular parasites that are capable of growth within cells in the host such as macrophages. The mycobacteria grow slowly, produce no endotoxin and are not motile. They multiply within the macrophages, kill the macrophage and are taken up by new macrophages to start the process over. Host resistance depends upon activation of the macrophages. Activated macrophages are able to kill the bacteria that reside within the cell. This activation depends upon specific T-cells which are produced as the result of a cell mediated immune reaction against proteins of the mycobacteria. Mycobacterial infections have been likened to a war of attrition in which there is a delicate balance between the ability of the mycobacteria to survive within the macrophages and the ability of the host to activate macrophages sufficiently to kill them. In the absence of rapidly acting antiinfective compounds, the goal of therapy is to tip the balance in favor of the host.

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

*Mycobacterium avium* bacilli occur in several distinct colony forms. Bacilli which grow as transparent or rough colonies on conventional laboratory media are able to multiply within macrophages in tissue culture, are virulent when injected into susceptible mice, and are resistant to antibiotics. Rough or transparent bacilli which are maintained on laboratory culture media often spontaneously assume an opaque colony morphology at which time they fail to grow in macrophages, are avirulent in mice, and are highly susceptible to antibiotics. The differences in colony morphology between the transparent, rough and opaque strains of *Mycobacterium avium* are almost certainly due to the presence of a glycolipid coating on the surface of transparent and rough organisms which acts as a protective capsule. This capsule, or coating, is composed primarily of C-mycosides which apparently shield the virulent *Mycobacterium avium* organisms from lysosomal enzymes and antibiotics. By contrast, the non-virulent opaque forms of *Mycobacterium avium* have very little C-mycoside on their surface. Both resistance to antibiotics and resistance to killing by macrophages have been attributed to the glycolipid barrier on the surface of *Mycobacterium avium.*

Fatty acids have been shown to exert either an inhibitory or enhancing effect on mycobacterial growth depending on the length of the carbon chain, the degree of saturation, and the presence and type of hydrophilic groups. The mechanism of the growth inhibition effect of fatty acids is not understood, but they are known to be surface-active agents which can interact with glycolipids on the surface of the mycobacteria.

Cornforth et al. ("Antituberculosis Effect of Certain Surface-Active Polyoxyethylene Ethers in Mice." *Nature*, 168; 150–153,1951) reported that certain nonionic surface active agents have antituberculosis effects in mice. Effective materials were arylalkyl polyether ethoxylates, Triton WR1339 and Triton A20. These agents are polymerized forms of familiar Triton surfactants. Mice injected intravenously with 15–25 milligrams of the material were protected from lethal challenge with virulent *Mycobacterium tuberculosis* organisms. The material could be injected before, or up to five days after injection of the organisms with mycobacteria. The untreated animals died within three weeks after injection. Over 80% of the treated animals survived at least three weeks with evidence of only minimal tuberculosis lesions.

Triton WR1339 and Triton A20 are mixtures of numerous similar compounds and are generally toxic. Cornforth and his colleagues synthesized a number of similar materials having greater purity, and found that the antituberculosis effect increased with the molecular weight of the hydrophobic portion of the molecules. The most effective pure preparation had four alkylphenol groups attached in a ring configuration. The size of the hydrophilic moiety was also important. Preparations with an average of 15 to 20 polyoxyethylene (POE) moieties per phenolic group were most effective in treating tuberculosis. However, increasing the number of POE moieties to 60 produced a compound which caused infection to progress more rapidly than untreated controls.

Numerous studies were performed to evaluate the mechanisms of the tuberculosis and antituberculosis effects of these compounds. The antituberculosis compounds were found to impede the growth of virulent tuberculosis bacteria in intact animals and in macrophages in tissue culture. However, they had no effect on the growth of the organisms in bacterial culture. Consequently, the agents affected either the host or the host-parasite interactions, but had no direct effect on mycobacteria. The bulk of evidence suggested that the tuberculosis and antituberculosis effects were due to modification of surface lipids of the mycobacteria.

The purified Cornforth compounds were not developed commercially as antimycobacterial agents. The reasons for this decision are not known, but several factors may have contributed. First, none of the preparations were pure. Second, the compounds suppressed the growth of mycobacteria in animals but did not produce cures. Finally, the compounds were found to be significantly toxic, producing disorders such as necrosis of the liver.

It is known that nonionic surfactants, in general, are much less toxic than either anionic or cationic surfactants. The nonionic block copolymers are among the least toxic of known surfactants. Nonionic block copolymer surfactants can be synthesized in forms which span virtually the entire range of physical chemical activities of known nonionic surface active agents. Wetting agents with properties reminiscent of Cornforth's antituberculosis agents can be produced in many molecular configurations. They can be produced in a higher molecular weight and in a purer form than is practically feasible with most other surfactants. Problems with toxicity of inactive contaminants can be minimized. The known effects of the block copolymers on serum lipids suggest that the block copolymers have biologic activities similar to those of the agents studied by Cornforth with less toxic effects.

Consequently, there is an immediate and increasing need for a new, safe and effective compound that will have an appropriate effect on mycobacteria organisms present in macrophages which does not exhibit excessive toxicity.

Acquired Immune Deficiency Syndrome, or AIDS, is a disease thought to be caused by a human retrovirus, the Human T Lymphotropic Virus III (HTLV-III) which is also called human immunodeficiency virus or HIV. Like other retroviruses, HIV has ribonucleic acid, or RNA, as its genetic material. When the virus enters the host cell, a viral enzyme called reverse transcriptase exploits the viral RNA as a template to assemble a corresponding molecule of DNA. The DNA travels through the cell nucleus and inserts itself among the host chromosomes, where it provides the basis for viral replication.

In the case of HIV, the host cell is often a T4 lymphocyte, a white blood cell that has a central and regulatory role in the immune system. Once it is inside a T4 cell, the virus may remain latent until the lymphocyte is immunologically stimulated by a secondary infection. Then the virus reproducing itself rapidly killing or rendering ineffective the host cell. The resulting depletion of the T4 cells, and loss of activity leaves the patient vulnerable to "opportunistic" infections by an agent that would not normally harm a healthy person. The virus damages the host by many other mechanisms as well.

Many therapies against AIDS infection that are currently being investigated. Several of these therapies under investigation are based on interrupting the reverse transcriptase as it assembles the viral DNA destined to become the virus. The drugs used for this purpose are chemical analogs of the nucleic acids that form the subunits of DNA. When the analog is supplied to an infected cell, reverse transcriptase will incorporate it into a growing DNA chain. Because the analog lacks the correct attachment point for the next subunit, however, the chain is terminated. The truncated DNA cannot integrate itself into the host chromosomes or provide the basis for viral replication, and so the spread of the infection is halted. One of the compounds that is thought to act by mimicking a nucleotide is azidothymidine, or AZT. However, AZT is known to have serious side effects and its efficacy in mitigating the AIDS disease has been questioned. The macrophage is now known to be an additional reservoir of the AIDS virus in the body.

Consequently, there is an immediate need for a compound that will suppress or halt the replication and infection of cells by the viruses such as the HIV virus. There is also a need for a compound with antiviral activity which can localize in macrophages. Further, what is needed is a composition that not only has an cidal effect on a wide variety of microorganisms, but can also facilitate the delivery of drugs or other agents into the cell.

SUMMARY OF THE INVENTION

In accordance with the present invention, a composition and method is provided that is effective in treating infections caused by microorganisms such as bacteria, fungi, viruses, and protozoa. The present invention is effective in inhibiting the growth of microorganisms such as Mycobacterium species including, but not limited to, *Mycobacterium avium-intracellulare* complex, *M. tuberculosis, Toxoplasma gondii,* HIV and human herpes viruses.

The antiinfective composition of the present invention comprises a surface active copolymer. The surface active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by ($C_3H_6O$) has a molecular weight of approximately 1,200 to approximately 15,000, preferably between approximately 1200 and approximately 5300, more preferably between approximately 1750 and approximately 4500, still more preferably approximately 2250 to approximately 4000, and b is an integer such that the hydrophile portion represented by ($C_2H_4O$) constitutes approximately 1% to approximately 50% by weight of the compound, preferably approximately 10% to approximately 50% by weight of the compound, more preferably approximately 5% to approximately 30%, and still more preferably approximately 5% to approximately 20%.

In addition, the present invention also comprises an antiinfective composition effective against infectious diseases comprising an injectable, topical, transdermal, oral, mucosal or inhalation dosage form of an effective amount of a drug, such as an antibiotic or other therapeutic agent, and an effective amount of a nonionic block copolymer having the following general formula:

$$HO(C_2H_4)_b(C_3H_6O)_a(C_2H_4O)_bH$$

wherein a is an integer such that the hydrophobe represented by ($C_3H_6O$) has a molecular weight of approximately 1,200 to approximately 15,000, preferably between approximately 1200 and approximately 5300, more preferably between approximately 1750 and approximately 4500, still more preferably approximately 2250 to approximately 4000, and b is an integer such that the hydrophile portion represented by ($C_2H_4O$) constitutes approximately 1% to approximately 50% by weight of the compound, preferably approximately 10% to approximately 50% by weight of the compound, more preferably approximately 5% to approximately 30%, and still more preferably approximately 5% to approximately 20%.

The composition of the present invention can be administered by a number of routes including, but not limited to injection, topical, transdermal, inhalation, trans-mucosal, oral ingestion, and a combination of a plurality of modes of administration. Additionally, the therapeutic drug may be administered separately from the block copolymers of the present invention, by the same or different route of administration, either simultaneously or at different times. The present invention provides a composition that can be administered to patients who are infected with Mycobacterium species. The surface active copolymer is effective in inhibiting the growth of Mycobacterium species and also causes the bacterium to be more susceptible to conventional antibiotics.

Accordingly, it is an object of the present invention to provide a compound which can be used to treat persons with infectious diseases.

Yet another object of the present invention is to provide a method of treating viral infections in humans or animals.

Another object of the present invention is a compound and method that is effective in inhibiting the replication of viruses in both animals and humans.

Another object of the present invention is to provide a compound and method that is effective in inhibiting the replication of HIV and other RNA and DNA viruses.

Yet another object of the present invention is to provide a method of treating bacterial infections in humans or animals.

Another object of the present invention is to provide a surfactant compound that can be used to treat mycobacterial infections in persons with AIDS.

Another object of the present invention is to provide a compound effective against protozoa and protozoal infections.

Another object of the present invention is to provide a compound and method that is effective in inhibiting fungal infections.

It is another object of the present invention to inactivate virus in a blood product prior to infusion into a person or animal.

Another object of the present invention is to provide a surfactant compound that can be used to prevent the development of tuberculosis in immunocompromised persons such as the elderly.

A further object of the present invention is to provide a surfactant compound that will inhibit the growth of *Mycobacterium avium intracellulare* complex.

Another object of the present invention is to provide an antibiotic surfactant compound that is non-toxic for humans.

Yet another object of the present invention is to provide a surfactant compound that causes the Mycobacterium species to be more susceptible to conventional antibiotics.

Another object of the present invention is to provide a composition that is effective against protozoa such as toxoplasma.

These and other objects, features and advantages of the present invention will become apparent after a review of the following detailed description of the disclosed embodiment and the appended claims.

BRIEF DESCRIPTION OF THE DRAWINGS

FIG. 14 is a graphical representation of the activity of CRL-8131 plus pyrimethamine in mice infected intraperitoneally with tachyzoites of strain RH of *T. gondii*.

FIG. 15 is a graphical representation of the activity of CRL-8131 plus sulfadiazine in mice infected intraperitoneally with tachyzoites of strain RH of *T. gondii*.

FIG. 16 is a graphical representation of the activity of CRL-8131 plus clindamycin in mice infected intraperitoneally with tachyzoites of strain RH of *T. gondii*.

FIG. 17 is a graphical representation of the activity of CRL-8131 plus pyrimethamine in mice infected orally with cysts of the $C_{56}$ strain of *T. gondii*.

DETAILED DESCRIPTION

Figure 1:
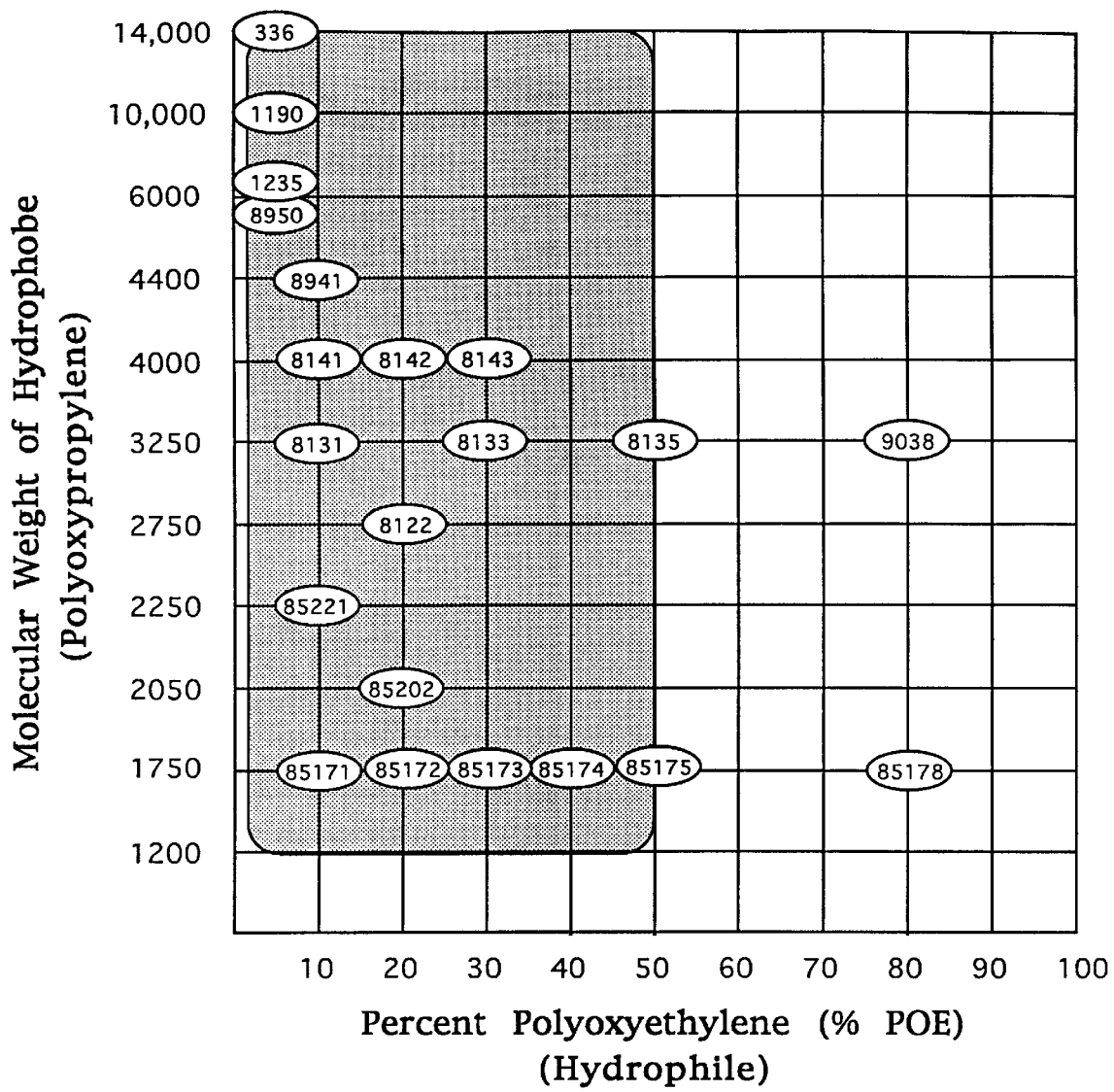
FIG. 1 is a grid illustrating block copolymers by molecular weight of hydrophobe and percent hydrophile.
Figure 2:
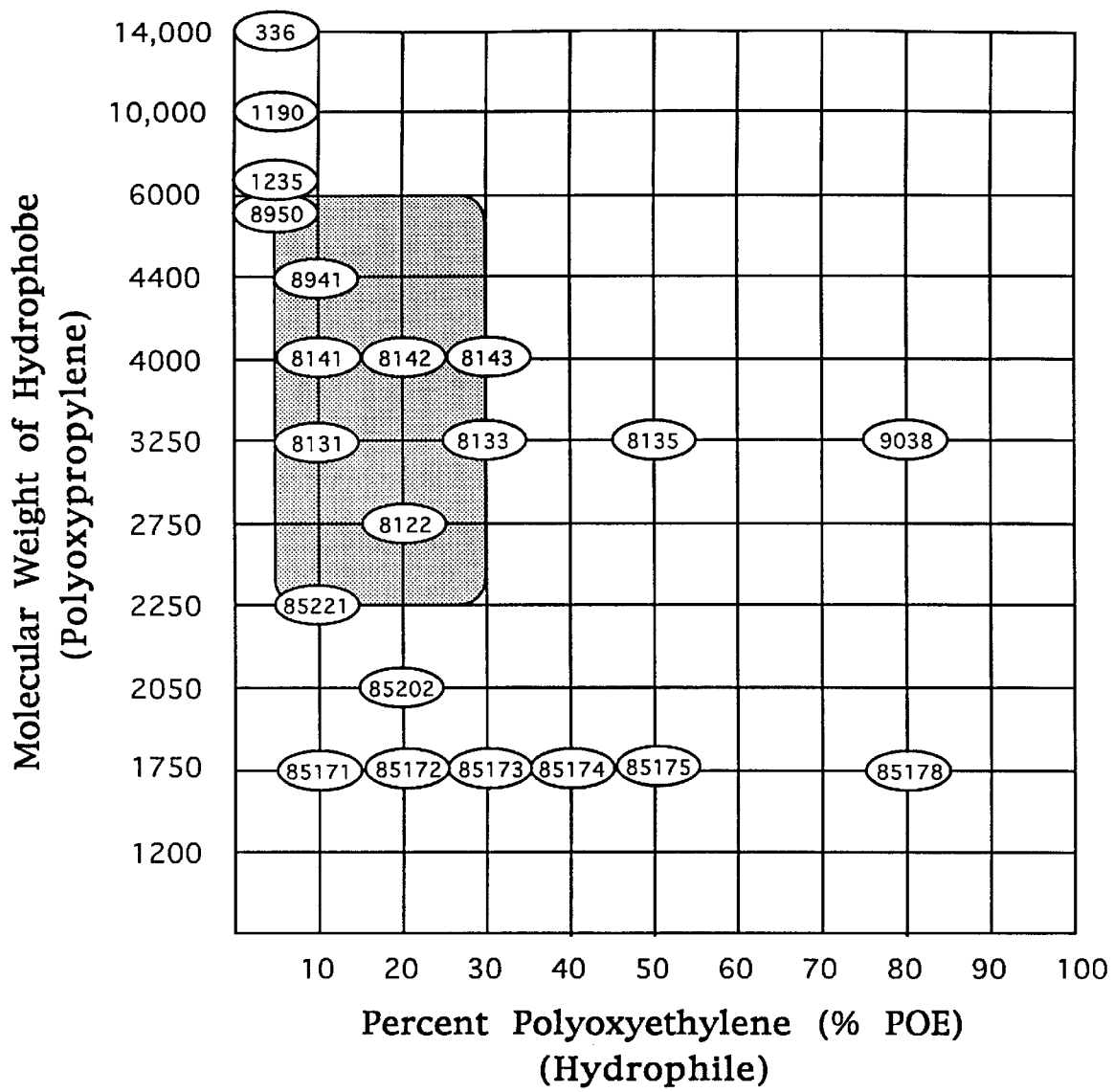
FIG. 2 is a grid illustrating preferred antiinfective block copolymers by molecular weight of hydrophobe and percent hydrophile.
Figure 3:
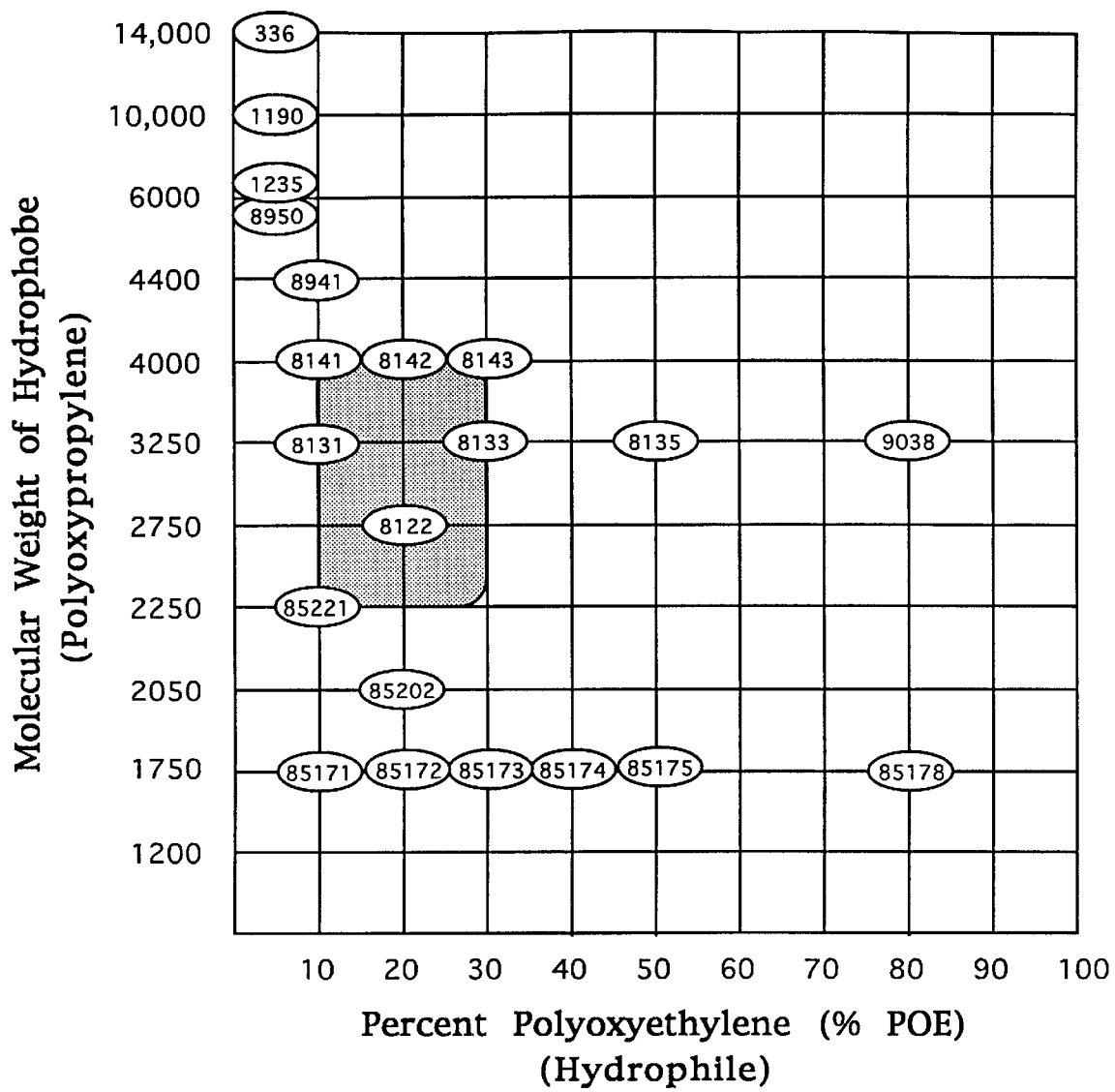
FIG. 3 is a grid illustrating other preferred antiinfective block copolymers by molecular weight of hydrophobe and percent hydrophile.
Figure 4:
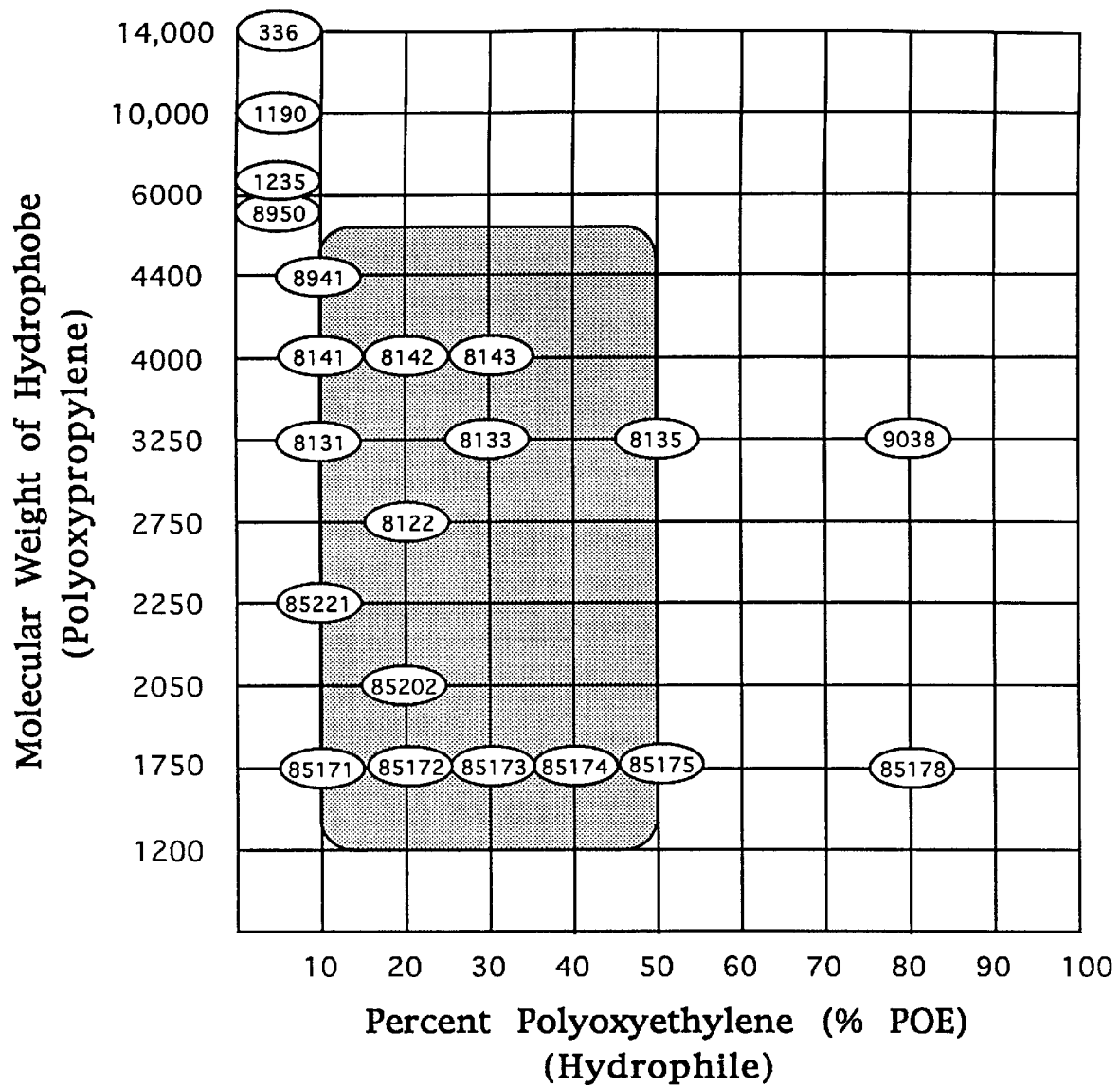
FIG. 4 is a grid illustrating yet other preferred antiinfective block copolymers by molecular weight of hydrophobe and percent hydrophile.
Figure 5:
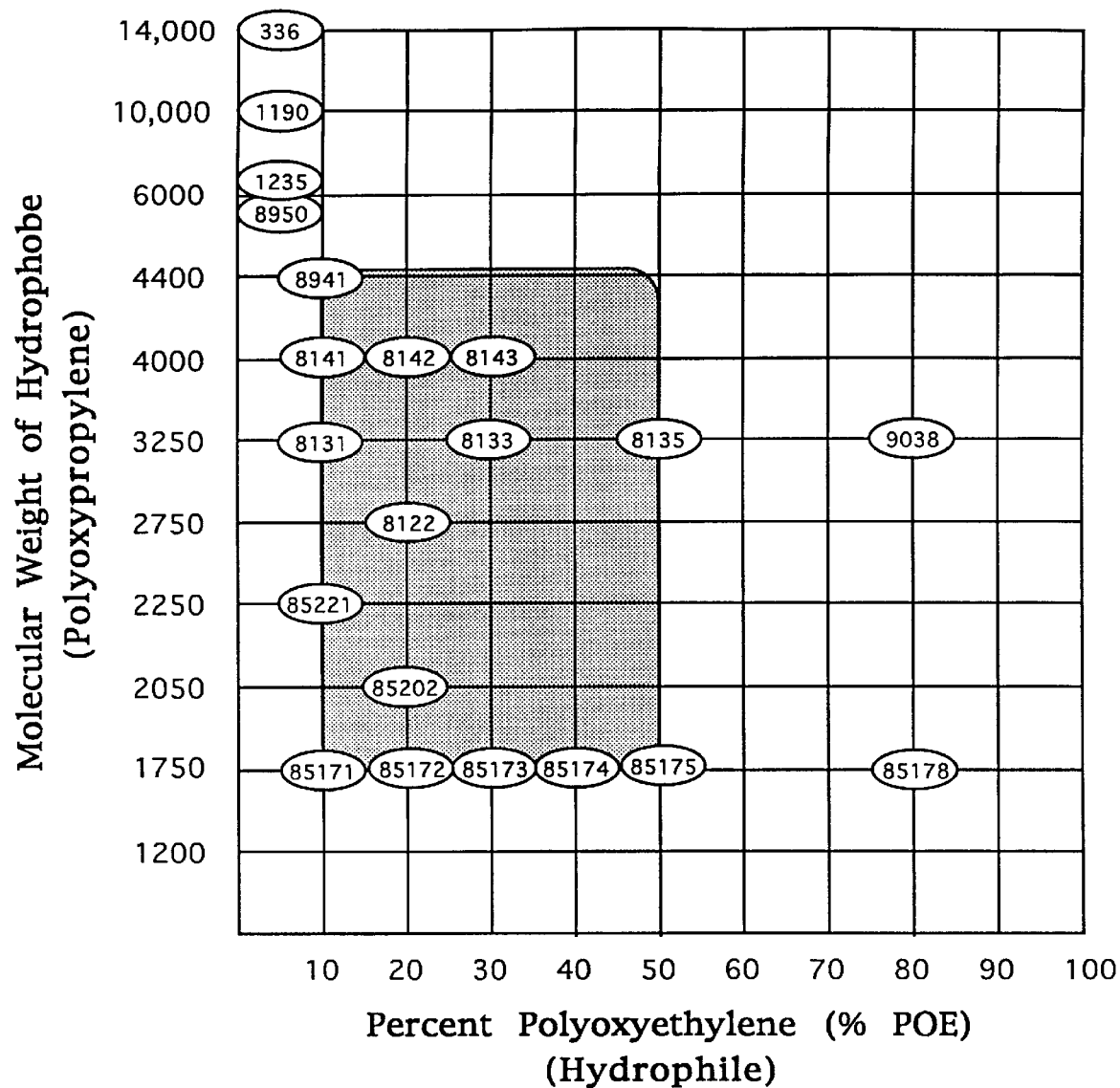
FIG. 5 is a grid illustrating still other preferred antiinfective block copolymers by molecular weight of hydrophobe and percent hydrophile.

The present invention comprises therapeutic compositions and methods which kill or inhibit the growth of microorganisms. An example of the bacteria that the present invention is effective against is mycobacteria species, such as *Mycobacterium tuberculosis, Mycobacterium avium,* and *Mycobacterium leprae*. Other microorganisms that the invention is effective against include, but are not limited to, *Chiamydia trachomatis, Chlamydia pneumoniae, Chlamydia psittaei Listeria monocytogenes, Candida albicans, Cryptococcus neoformans, Toxoplasma gondii, Pneumocystis carinii, Herpes simplex* virus type 1, Cytomegalovirus, influenza virus type A and B, and respiratory syncytial virus The present invention also includes therapeutic compositions and methods for treating DNA viruses and RNA viruses, and infections and infectious diseases caused by such viruses in a human or animal, including infections caused by HIV or herpes (such as HSV-1) or antigenically-related strains thereof. Antigenically-related strains are strains that cross react with antibodies specific for HIV. One skilled in the art can readily determine viral strains that are antigenically-related to HIV by conducting standard immunoassay tests using anti-HIV antibodies and the viral strain to be analyzed, and looking for positive cross-reactivity.

The surface active copolymers disclosed herein are effective in inhibiting or suppressing the replication of such viruses in cells.

The present invention also includes a therapeutic composition useful for delivering antimicrobial drugs and treating disease states comprising an admixture of a nonionic block copolymer and an antibiotic or therapeutic drug. Drugs that can be used with the nonionic copolymers of the present invention include, but are not limited to, rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, AZT, DDI, DDC, and other antiviral nucleoside analogs, foscornat, ganciclovir, viral protease inhibitors, antisense and other modified oligonucleotides, and ribavirin.

Preferred drugs to use for various infectious microorganisms are listed in Table I.

TABLE I

| Organism | Drugs |
| --- | --- |
| Bacteria | |
| *Mycobacterium tuberculosis* | Isoniazid, rifampin, ethambutol, pyrazinamide, streptomycin, clofazimine, rifabutin, fluoroquinolones such as ofloxacin and sparfloxacin |
| *Mycobacterium avium* | Rifabutin, rifampin, azithromycin, clarithromycin, fluoroquinolones |
| *Mycobacterium leprae* | Dapsone |
| *Chlamydia trachomatis* | Tetracycline, doxycyline, erythromycin, ciprofloxacin |
| *Chlamydia pneumoniae* | Doxycycline, erythromycin |
| *Listeria monocytogenes* | Ampicillin |
| Fungi | |
| *Candida albicans* | Amphotericin B, ketoconazole, fluconazole |
| *Cryptococcus neoformans* | Amphotericin B, ketoconazole, fluconazole |
| Protozoa | |
| *Toxoplasma gondii* | Pyrimethamine, sulfadiazine, clindamycin, azithromycin, clarithromycin, atovaquone |
| *Pneumocystis carinii* | Pentamidine, atovaquone |
| *Cryptosporidium sp.* | Paromomycin, diclazaril |
| Virus | |
| Herpes simplex virus type 1 and type 2 | Acyclovir, trifluorouridine and other antiviral nucleoside analogs, foscornat, antisense oligonucleotides, and triplex-specific DNA sequences |
| Cytomegalovirus | Foscarnet, ganciclovir |
| HIV | AZT, DDI, DDC, foscarnat, viral protease inhibitors, peptides, antisense oligonucleotides, triplex and other nucleic acid sequences |
| Influenza virus type A and B | Ribavirin |
| Respiratory syncytial virus | Ribavirin |
| Varizella zoster virus | Acyclovir |

Optionally, surfactants and low molecular weight alcohols are added to the therapeutic admixture of antimicrobial drug and nonionic block copolymer. Examples of surfactants useful in the present invention include Tween 80 and emulsions with fatty acids such as phospholipids, cholate and amino acids. The preferred surfactant is Tween 80. Surfactants are added to the admixture at a concentration ranging from approximately 0.1% to approximately 5% v/v. The preferred surfactant concentration is approximately 2%. The term "approximately" as it applies to concentrations expressed herein means the stated concentration plus or minus ten percent. The term "low molecular weight alcohols" means alcohols having two to eight carbons. An example of a low molecular weight alcohols useful in the present invention is ethanol, which is the preferred low molecular weight alcohol. Low molecular weight alcohols are added to the admixture at a concentration ranging from approximately 0.5% to approximately 5% v/v. The preferred low molecular weight alcohol concentration is between approximately 1% and approximately 3%.

The present invention comprises a surface active copolymer that is preferably an ethylene oxide-propylene oxide condensation product with the following general formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1,200 and approximately 15,000, and b is an integer such that the hydrophile portion represented by ($C_2H_4O$) constitutes approximately 1% to approximately 50% by weight of the compound.

Preferred embodiments of the copolymers of the present invention have the following general characteristics.

The antiinfective composition of the present invention comprises a surface active copolymer. The surface active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by ($C_3H_6O$) has a molecular weight of approximately 1,200 to approximately 15,000, preferably between approximately 1200 and approximately 5300, more preferably between approximately 1750 and approximately 4500, still more preferably approximately 2250 to approximately 4000, and b is an integer such that the hydrophile portion represented by ($C_2H_4O$) constitutes approximately 1% to approximately 50% by weight of the compound, preferably approximately 10% to approximately 50% by weight of the compound, more preferably approximately 5% to approximately 30%, and still more preferably approximately 5% to approximately 20%.

In addition, the present invention also comprises an antiinfective composition effective against infectious diseases comprising an injectable, topical, transdermal, transmucosal, oral, mucosal or inhalation dosage form of an effective amount of a drug, such as an antibiotic or other therapeutic antimicrobial agent, admixed with an effective amount of a nonionic block copolymer having the following general formula:

$$HO(C_2H_4O)_b(C_3H_6O)_a(C_2H_4O)_bH$$

wherein a is an integer such that the hydrophobe represented by ($C_3H_6O$) has a molecular weight of approximately 1,200 to approximately 15,000, preferably between approximately 1200 and approximately 5300, more preferably between approximately 1750 and approximately 4500, still more preferably approximately 2250 to approximately 4000, and b is an integer such that the hydrophile portion represented by ($C_2H_4O$) constitutes approximately 1% to approximately 50% by weight of the compound, preferably approximately 10% to approximately 50% by weight of the compound, more preferably approximately 5% to approximately 30%, and still more preferably approximately 5% to approximately 20%. An effective amount is an amount sufficient to treat an infected human or animal by reducing the number of infectious microbes, and/or inhibiting the ability of the infectious microbes to produce toxins and/or reproduce and multiply.

It should be understood that the molecular weight and percentage ranges that are described for the block copolymer are to be considered outside ranges and that any population of molecules that falls within the stated ranges may be considered an embodiment of the present invention.

The entire block copolymer molecule is poorly soluble in water and is substantially nonionic. The steric configurations and physiochemical properties of the molecule, rather than the chemical nature of the constituent parts, are believed to be largely responsible for the antiinfective activity and therapeutic delivery activity. Compositions of the present invention include, but are not limited to aqueous solutions, suspensions or emulsions, such as oil-in-water emulsions.

The polymer blocks are formed by condensation of ethylene oxide and propylene oxide, at elevated temperature and pressure, in the presence of a catalyst. There is some statistical variation in the number of monomer units which combine to form a polymer chain in each copolymer. The molecular weights given are approximations of the average weight of copolymer molecules in each preparation and are dependent on the assay methodology and calibration standards used. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619, which is incorporated herein by reference in its entirety. (Also see, "A Review of Block Polymer Surfactants", Schmolka I. R., *J. Am. Oil Chemist Soc.*, 54:110–116 (1977) and *Block and Graft Copolymerization*, Volume 2, edited by R. J. Ceresa, John Wiley and Sons, New York, 1976.

Ethylene oxide-propylene oxide condensation products which may be employed in the present invention are summarized in Table II. It is to be understood that these compounds are merely representative of the compounds that can be used to practice the present invention and do not include all possible compounds that could be used to practice the present invention. The high molecular weight copolymers listed in Table II that do not have a BASF tradename are novel compositions that have never been synthesized before.

TABLE II

| CRL # | Poloxamer | BASF Trade Name | Molecular Weight of POP | % POE |
| --- | --- | --- | --- | --- |
|  | 122 | L42 | ≈1200 | ≈20% |
| CRL-85171 | 181 | L61 | ≈1750 | ≈10% |
| CRL-85172 | 182 | L62 | ≈1750 | ≈20% |
| CRL-85173 | 183 | L63 | ≈1750 | ≈30% |
| CRL-85174 | 184 | L64 | ≈1750 | ≈40% |
| CRL-85175 | 185 | P65 | ≈1750 | ≈50% |
| CRL-85178 | 188 | F68 | ≈1750 | ≈80% |
| CRL-85202 | 212 | L72 | ≈2050 | ≈20% |
| CRL-85221 | 231 | L81 | ≈2250 | ≈10% |
| CRL-8122 | 282 | L92 | ≈2750 | ≈20% |
| CRL-8131 | 331 | L101 | ≈3250 | ≈10% |

TABLE II-continued

| CRL # | Poloxamer | BASF Trade Name | Molecular Weight of POP | % POE |
|---|---|---|---|---|
| CRL-8133 | 333 | P103 | ≈3250 | ≈30% |
| CRL-8135 | 335 | P105 | ≈3250 | ≈50% |
| CRL-9038 | 338 | F108 | ≈3250 | ≈80% |
| CRL-8141 | 401 | L121 | ≈4000 | ≈10% |
| CRL-8142 | 402 | L122 | ≈4000 | ≈20% |
| CRL-8143 | 403 | P123 | ≈4000 | ≈30% |
| CRL-8941 | 441 | L141 | ≈4400 | ≈10% |
| CRL-8950 | — | — | ≈6000 | ≈5% |
| CRL-1235 | — | — | ≈7500 | ≈5% |
| CRL-1190 | — | — | ≈10,000 | ≈5% |
| CRL-336 | — | — | ≈14,000 | ≈5% |
| CRL-1183 | — | — | ≈3750 | ≈10% |
| CRL-1122 | — | — | ≈5900 | ≈12% |
| CRL-3362 | — | — | ≈3900 | ≈11% |
| CRL-3632 | — | — | ≈4740 | ≈11% |
| CRL-9352 | — | — | ≈7750 | ≈15% |
| CRL-1187 | — | — | ≈750 | ≈25% |

A grid illustrating the range of copolymers encompassed by the present invention based upon the molecular weight of the hydrophobe portion and the percent hydrophile, and showing selected nonionic block copolymers appears as FIG. 1.

It has been discovered that the copolymers most effective as antiinfectives fall within the indicated regions of the copolymer grid as shown in FIGS. 2, 3, 4, and 5.

A preferred ethylene oxide-propylene oxide copolymer for use in the antiinfective composition of the present invention is a copolymer having the following formula:

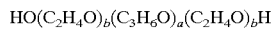

wherein a is an integer such that the hydrophobe represented by $(C_3H_6O)$ has a molecular weight of about 1,750 to 4,500 and b is an integer such that the hydrophile portion represented by $(C_2H_4O)$ constitutes approximately 10% to 40% by weight of the compound.

An especially preferred embodiment of the antiinfective compound of the present invention is the compound designated CRL-8133 with the following general formula:

$$HO(C_2H_4O)_b(C_3H_6O)_a(C_2H_4O)_bH$$

wherein the mean aggregate molecular weight of the hydrophobic portion of the triblock copolymer, consisting of polyoxypropylene (POP) is approximately 3,250 daltons; the hydrophile portion represented by polyoxyethylene (POE) constitutes approximately 30% of the total molecular weight of the compound.

Another especially preferred embodiment of the antiinfective compound of the present invention is the compound designated CRL-8131 with the following general formula:

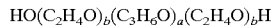

wherein the mean aggregate molecular weight of the hydrophobic portion of the triblock copolymer, consisting of polyoxypropylene (POP) is approximately 3,250 daltons; the hydrophile portion represented by polyoxyethylene (POE) constitutes approximately 10% of the total molecular weight of the compound.

Yet another especially preferred embodiment of the antiinfective compound of the present invention is the compound designated CRL-8142 with the following general formula:

wherein the mean aggregate molecular weight of the hydrophobic portion of the triblock copolymer, consisting of polyoxypropylene is approximately 4,000 daltons; the hydrophile portion represented by polyoxyethylene (POE) constitutes approximately 20% of the total molecular weight of the compound.

Still another especially preferred embodiment of the antiinfective compound of the present invention is the compound designated CRL-8143 with the following general formula:

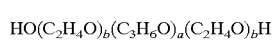

wherein the mean aggregate molecular weight of the hydrophobic portion of the triblock copolymer, consisting of polyoxypropylene is approximately 4,000 daltons; the hydrophile portion represented by polyoxyethylene (POE) constitutes approximately 30% of the total molecular weight of the compound.

The antiinfective compound of the present invention is effective in suppressing the growth of *Mycobacterium avium, Mycobacterium tuberculosis, Herpes simplex* virus type 1 and type 2, *Toxoplasmi gondii* and other microorganisms affecting humans and animals causing a variety of health disorders. The disorders in which the antiinfective compound of the present invention are effective include, but are not limited to bacterial infections, fungal infections, protozoal infection and viral infections. Examples of specific diseases include tuberculosis, toxoplasmosis, and AIDS. Other diseases caused by microorganisms will be obvious to one of skill in the art.

The antiinfective compositions of the present invention have been shown to be effective with only one administration to the patient. However, in certain cases, subsequent administrations may be necessary to achieve maximum efficiency. The mode of administration can be topical, transdermal, trans-mucosal, oral, inhalation, subcutaneous, intramuscular or intravenous. The preferred mode of injection is intravenous. The optimum amount of the antiinfective compound in an injection varies with the weight of the patient being treated, but appears to be in the range of $1\times10^{-3}$ M to $1\times10^{-4}$ M. The effective dose range generally includes dosages of 0.1 mg/Kg/day to 50 mg/Kg/day. A preferred dosage range is 0.5 mg/Kg/day to 25 mg/Kg/day. A more preferred dosage range is 1 mg/Kg/day to 10 mg/Kg/day. It has been surprisingly found that effective therapy is provided even when the block copolymer and the therapeutic drug are administered separately, either by the same or different routes of administration, and either simultaneously or at different times.

Non-ionic block copolymers form micelles above their critical micelle concentration. The non-ionic copolymers have negative thermal coefficients of solubility. In the cold, the kinetic energy of water molecules is reduced and they form weak hydrogen bonds with the oxygen of the POP blocks. This hydration of the hydrophobe promotes solubility at low temperatures. As the temperature rises, the "cloud point" is reached; the increased kinetic energy of the water breaks the hydrogen bonds, the polymer becomes insoluble and micelles form.

Thus, the copolymers can form physical structures that can be combined or loaded with an additional, distinct therapeutic agent. Consequently, the nonionic block copolymers of the present invention can be used as therapeutic drug delivery vehicles. Admixtures of therapeutic drugs with non-ionic block copolymers have the advantage of synergistic activity of two therapeutic agents. Further, copolymers having specific characteristics can be selected for use with particular therapeutic drugs. For example, CRL-8131, which is hydrophobic, is an excellent carrier for hydrophobic antibiotics such as rifampin. However, other agents which are not distinctly hydrophobic can be used according to the present invention.

A therapeutic delivery composition is prepared using any of the antiinfective block copolymers of the present invention in combination with any of a variety of antimicrobial agents. In a preferred embodiment CRL-8131 is used in a concentration of approximately 3% to approximately 5% to construct a therapeutic delivery vehicle. Therapeutic delivery vehicles made using copolymers that are more hydrophilic than CRL-8131 normally require a higher concentration (approximately 5% to approximately 10%) of the copolymer.

Using copolymer-based micelles as a therapeutic drug delivery vehicles is particularly desirable because the micelles are accumulated readily and are present for an extended period of time, in macrophages, the site of HIV and other viral infections and a major target for viral therapy. Examples of such therapeutic copolymer-based therapeutic compositions include CRL-8131 combined with 2% Tween 80 and 1% ethanol, and CRL-8142 combined with 1% Tween 80 and 5% ethanol.

Alternatively, nonionic block copolymers and therapeutic drugs may be administered to a human or animal separately, either simultaneously or at different times. For example, copolymers such as CRL-8131 or CRL-8142 are administered by injection, followed by administration of the therapeutic drug. Administration of the drug may be by any normal route such as, injection, topical or transdermal application, trans-mucosal absorption, inhalation or oral ingestion.

The following specific examples illustrate various aspects of the invention, such as in vitro suppression of the growth of colonies of *Mycobacterium avium* and HIV virus in vitro isolated from humans. Several of the examples also illustrate the invention as it applies to the suppression of growth of *Mycobacterium avium* and *Toxoplasma gondii* in macrophages. Still other examples illustrate the compositions and methods of the invention useful for gene therapy, and compositions and methods of the invention useful for gene-mediated immunization It will be appreciated that other embodiments and uses will be apparent to those skilled in the art and that the invention is not limited to these specific illustrative examples.

EXAMPLE I

Smooth transparent (virulent) and smooth domed (nonvirulent) colonies of *Mycobacterium avium* derived from the same patient isolate were grown in $7H_{12}$ Middlebrook broth (Johnston Laboratories, Cockeysville, Md.). The Bactec $7H_{12}$ Middlebrook TB medium is an enriched Middlebrook $7H_9$ broth base which has been supplemented with bovine serum albumin (fraction V), catalase, casein hydrolysate and $^{14}C$-labeled fatty acids. Mycobacteria metabolize the 14C-labeled substrates and release $CO_2$ in air, thereby maintaining the recommended atmosphere. In addition, vials were inoculated with antimycobacterial agents and *M. tuberculosis* so that the evolution of $CO_2$ can be correlated to the susceptibility or resistance of the organism to the drug. When the mycobacteria grow in the medium containing $^{14}C$-labeled fatty acid, they utilize the fatty acid and $CO_2$ is produced. The production of $CO_2$ can be detected quantitatively, reflecting the rate and amount of growth occurring in the vial, and is expressed in terms of the "growth index". If an anti-tuberculosis drug is added to the medium, suppression of growth occurs in the case of susceptible organisms which can be detected by either a decline or a very small increase of the growth index as compared to the control. However, if the organisms are resistant, no suppression occurs in the rate of increase of the growth index on daily testing.

To determine the 1% proportion of resistance, the inoculum in the control vial is one hundred fold less than the inoculum used for drug containing vials. Growth index readings are taken each day after inoculation and the increase in growth index over that of the previous day, is compared for the control vial and the vials containing drugs. If the daily increase in growth index, called delta growth index, in the drug vial is equal to or greater than that in the control vial, the test organisms are considered resistant to the drug. For a susceptible organism, the daily increase in the growth index for the control would be much higher than for the drug vial.

Cultures were incubated at 36° C. and checked daily with a Bactec 460TB (Johnston Laboratories, Cockeysville, Md.) instrument with a self-contained laminar flow hood. A growth index was determined by measuring the amount of $^{14}C$ released into the atmosphere of the container as a result of mycobacterial utilization of $^{14}C$-labeled fatty acids.

*Mycobacterium avium* organisms were treated with one of four nonionic block copolymers, designated CRL-8131, CRL-8133, CRL-8135, and CRL-9038. These copolymers have identical hydrophobic portions and differ only in the length of the polyoxyethylene (hydrophilic) chains. These four molecules range in size from 3,600 to 14,000 daltons and the molecular weight attributable to the polyoxypropylene portion of each molecule is approximately 3,250. The hydrophilic portion of each molecule is 10% for CRL-8131, 30% for CRL-8133, 50% for CRL-8135, and 80% for CRL-9038. Each of the candidate anti-mycobacterial copolymers were mixed with the Middlebrook tuberculosis medium at concentration of $1\times10^{-3}M$ and $1\times10^{-4}M$.

Figure 6:
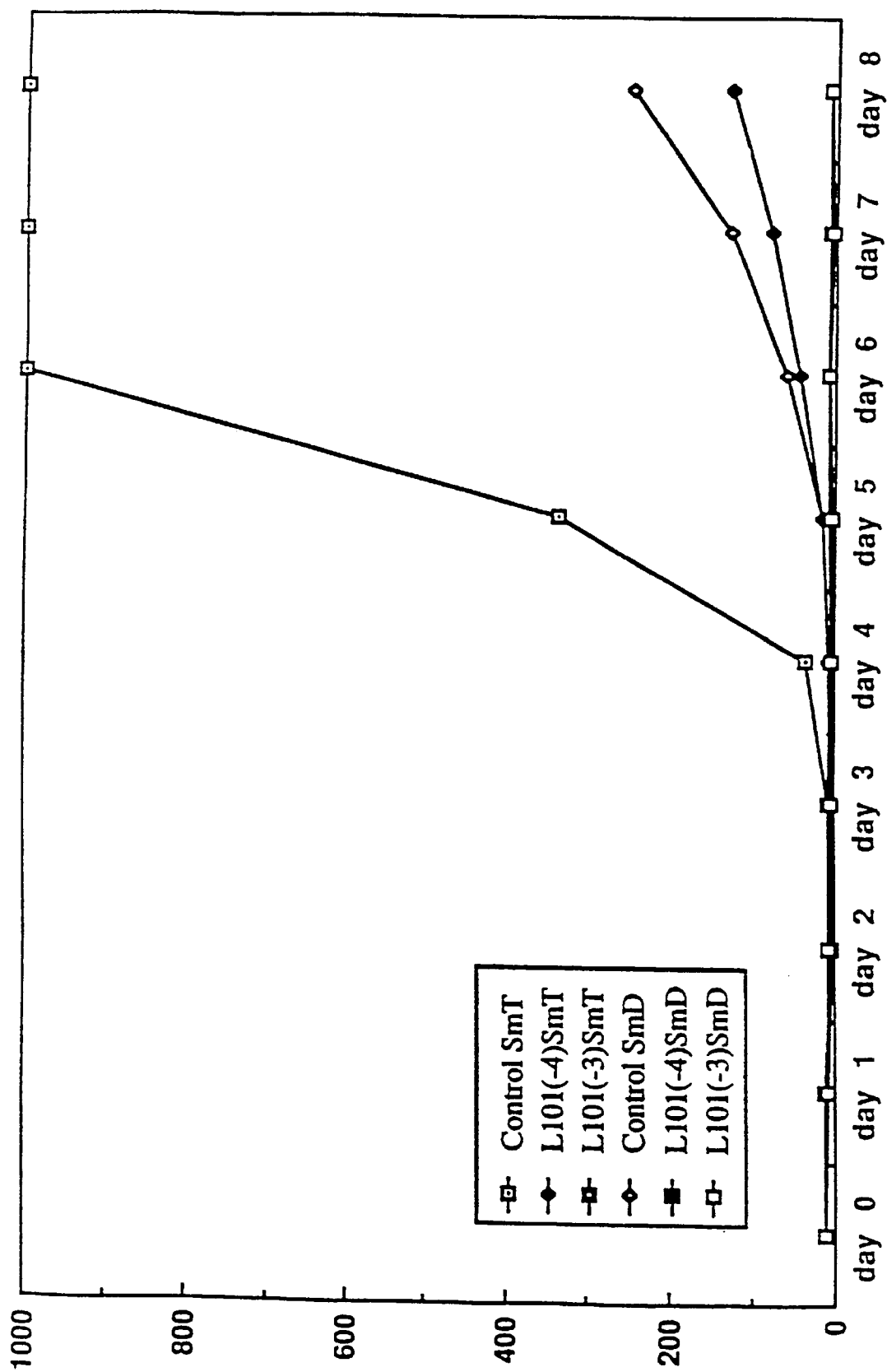
FIG. 6 is a graphical representation of the effect of CRL-8131 on the growth of *Mycobacterium avium*.
Figure 7:
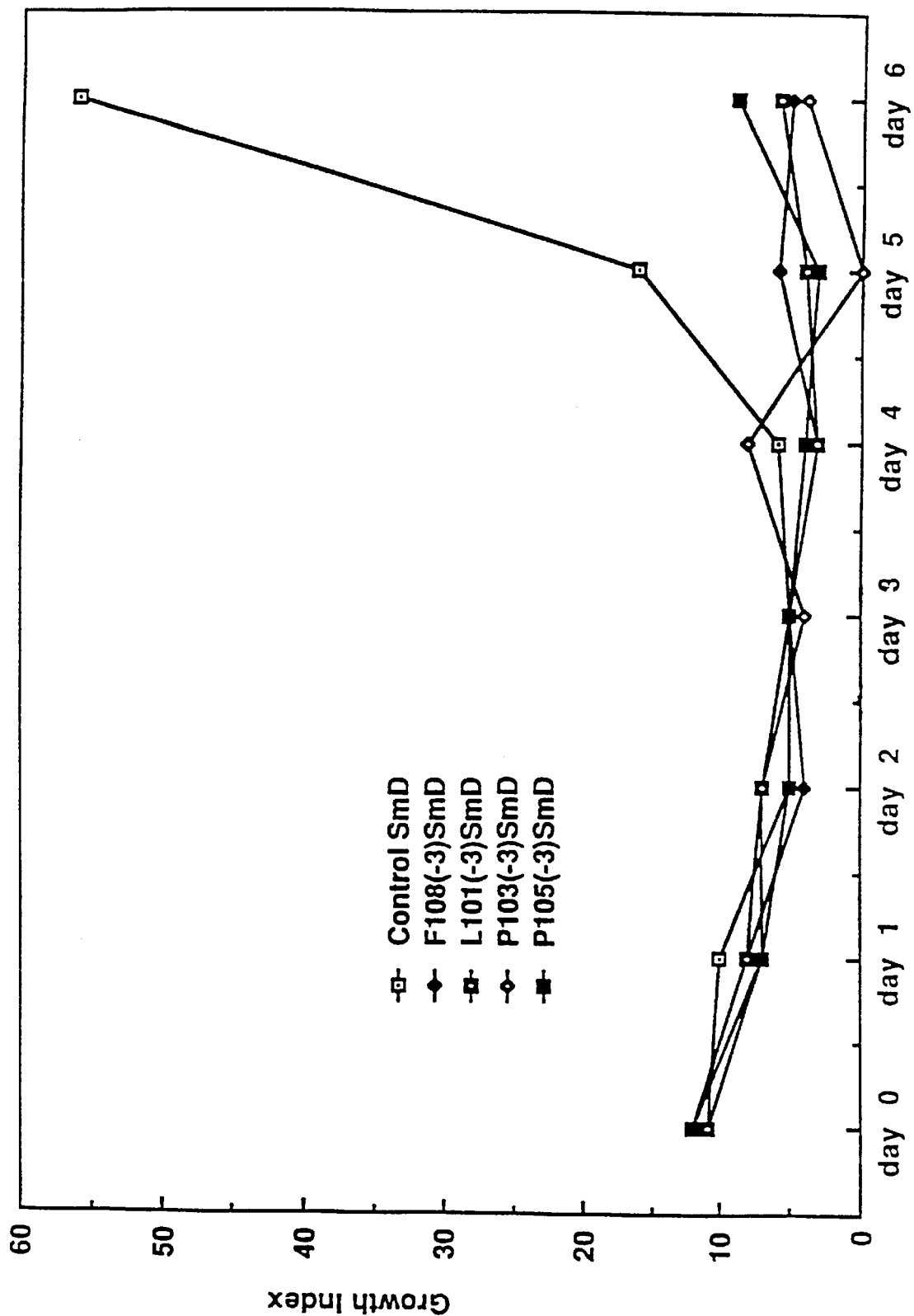
FIG. 7 is a graphical representation of the effect of CRL-9038, CRL-8131, CRL-8133 and CRL-8135 on the growth of *Mycobacterium avium*.
Figure 8:
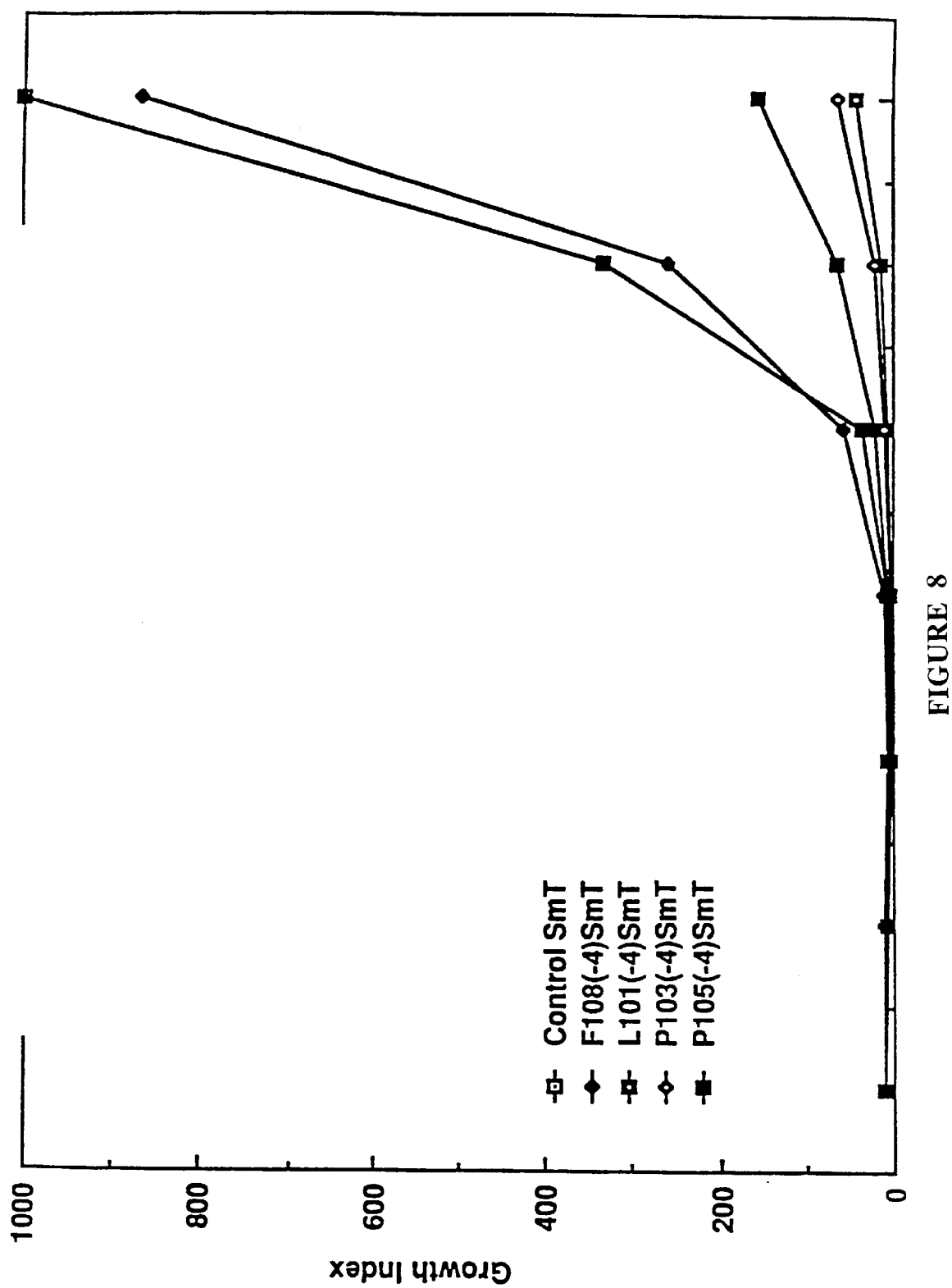
FIG. 8 is a graphical representation of the effect of CRL-8131, CRL-8133, and CRL-8135 on the growth of *Mycobacterium avium*.
Figure 9:
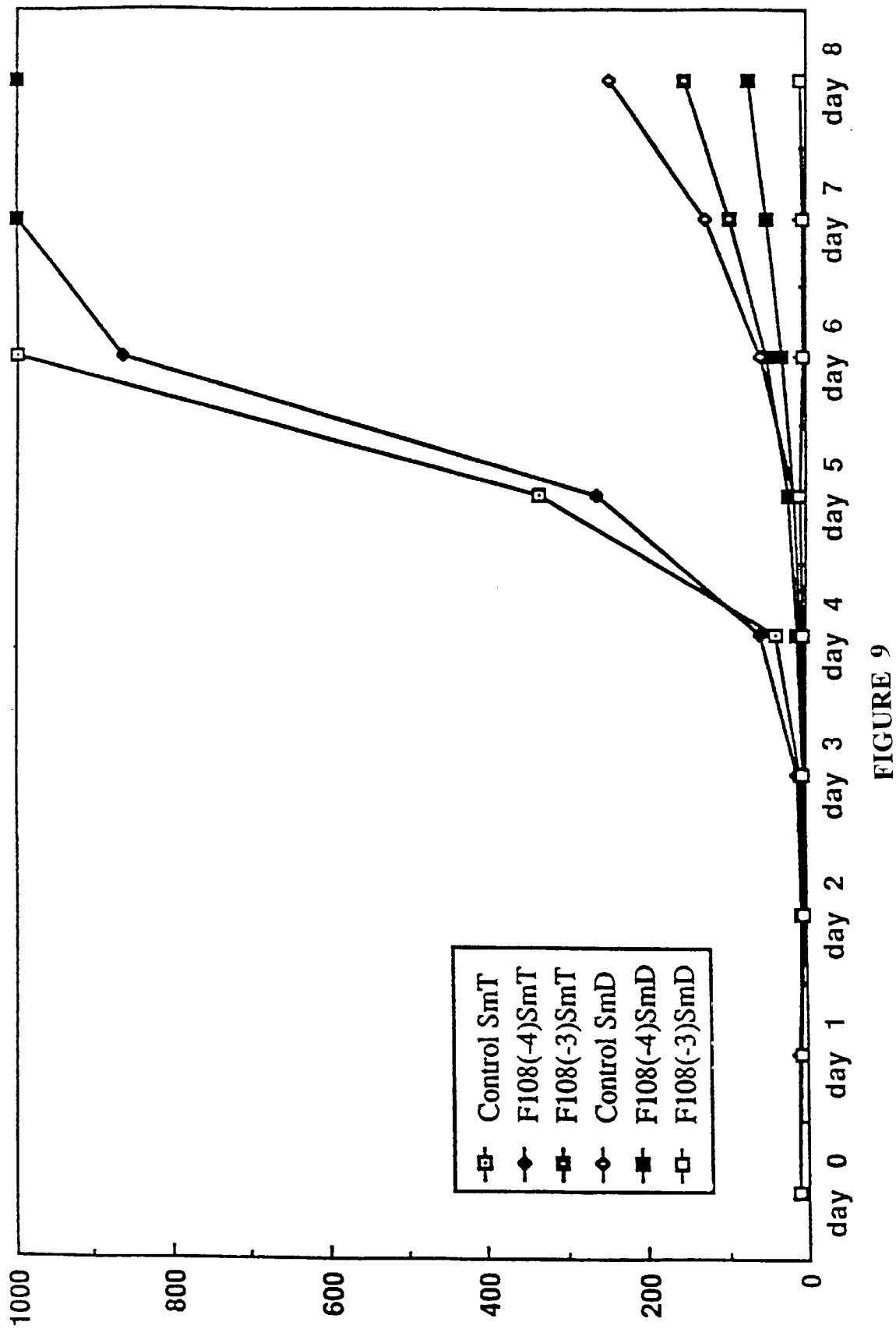
FIG. 9 is a graphical representation of the effect of CRL-9038 on the growth of *Mycobacterium avium*.

As shown in FIGS. 6, 7, and 8, a significant reduction in growth rate of both smooth transparent (SmT) and smooth domed (SmD) colonies treated with CRL-8131, CRL-8133, and CRL-8135 occurred. As shown in FIG. 9, smooth transparent (virulent) colonies treated with CRL-9038 in a concentration of $1\times10^{-4}M$ did not inhibit the growth of *Mycobacterium avium;* however, an CRL-9038 concentration of $1\times10^{-3}M$ showed some suppression of bacterial growth.

EXAMPLE II

Smooth transparent (virulent) and smooth domed (nonvirulent) colonies of *Mycobacterium avium* derived from the same patient isolate were grown in $BACTEC_7H_{12}$ Middlebrook broth. A growth index was determined by measuring the amount of $^{14}C$ released into the atmosphere of the container as a result of mycobacterial utilization of $^{14}C$-labeled fatty acid as described in Example I.

*Mycobacterium avium* organisms treated with one of fourteen nonionic block copolymers, designated L42, CRL-85171, CRL-85172, CRL-85173, CRL-85174, CRL-85175, CRL-85202, CRL-85221, CRL-8122, CRL-8131, CRL-8133, CRL-8141, CRL-8142, and CRL-8143. Each copolymer has a polyoxyethylene portion ranging from 5% to 50% of the total molecule. The molecular weight of the polyoxypropylene portion of each molecule ranges from approximately 1,200 to approximately 4,000. The physical characteristics of each copolymer are summarized in Table II.

Figure 10:
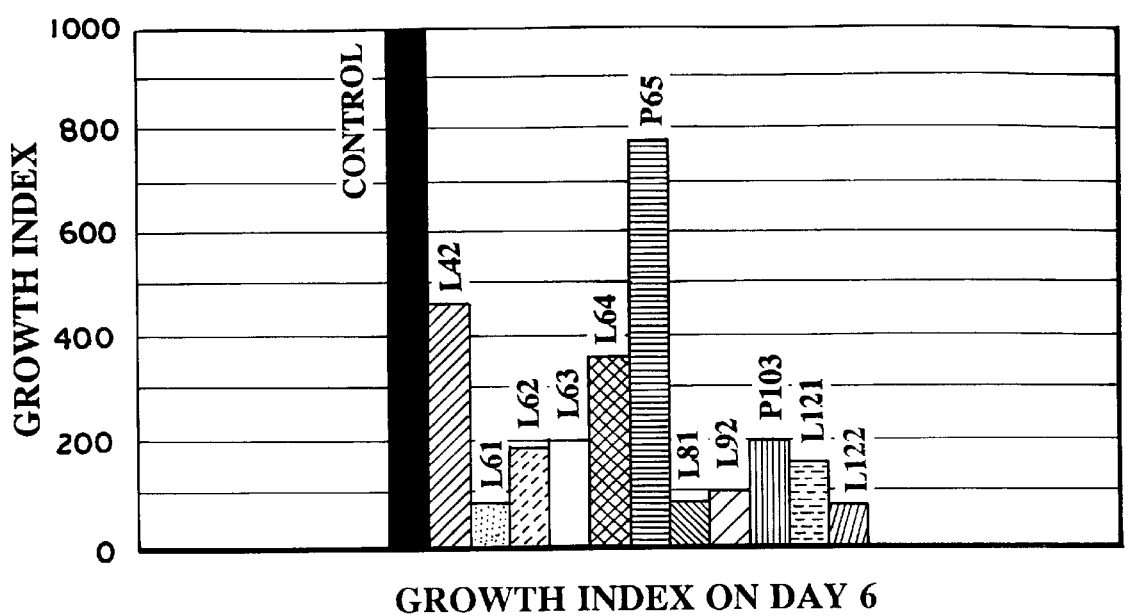
FIG. 10 is a graphical representation of the effect of 11 nonionic copolymers on the growth of *Mycobacterium avium*.

As shown in FIG. 10, there was a significant reduction in growth rate of smooth transparent colonies treated with all the copolymers tested. CRL-85175 and L42 exhibited only moderate inhibition.

EXAMPLE III

Figure 11:
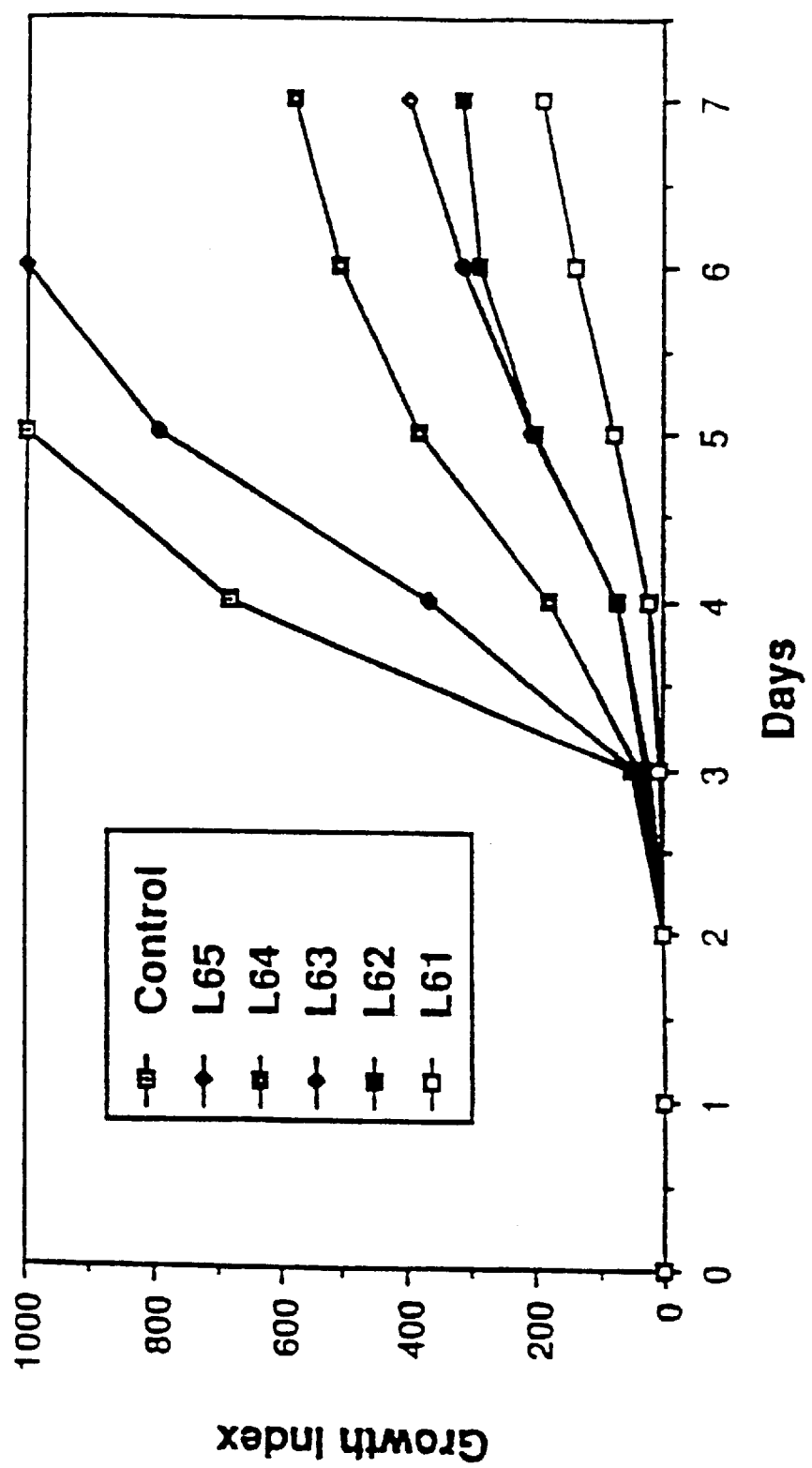
FIG. 11 is a graphical representation of the effect of several non-ionic copolymer on *Mycobacterium avium* growth.
Figure 12:
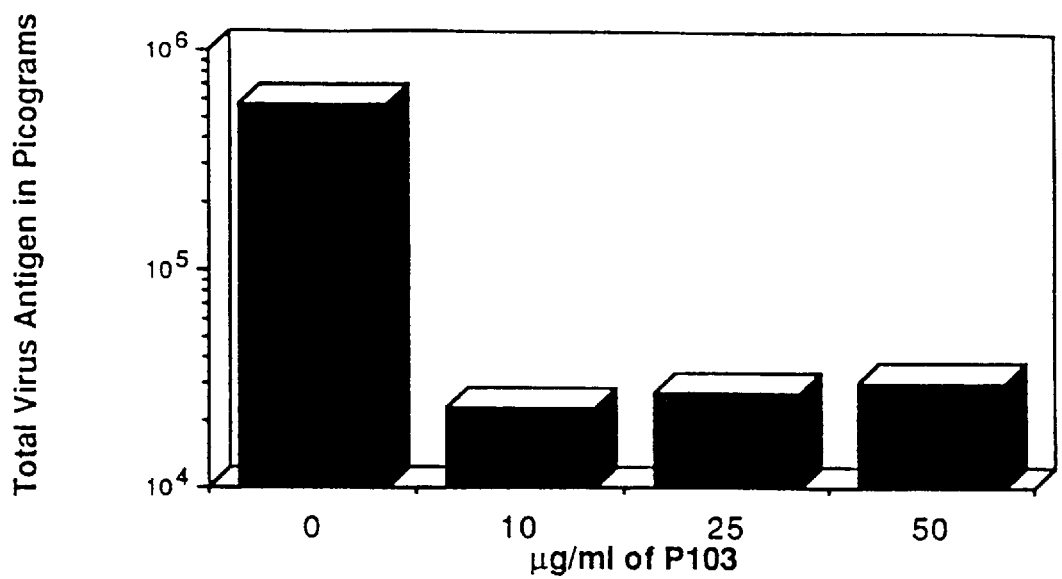
FIG. 12 is a graphical representation of the effect of the CRL-8133 copolymer on HIV infection in $H_9$ cells.

A correlation between increasing hydrophobicity of the copolymer and inhibition of *M. avium* growth is shown in FIG. 11. The copolymers having a polyoxypropylene molecular weight of 1750 were tested for inhibition of *M. avium.* The copolymers tested are CRL-85171, CRL-85172, CRL-85173, CRL-85174, and CRL-85175.

As shown in FIG. 11, inhibition of mycobacterial growth specifically correlates with the molecular structure of the copolymers. The low molecular weight copolymers which have only a small percentage of hydrophil appear to inhibit *M. avium* growth more than copolymers which are more hydrophilic.

EXAMPLE IV

The effectiveness of P103 copolymer is examined in preventing HIV replication in $H_9$ cells using a high multiplicity of viral infection. The infections are conducted in the following manner: $10^5$ $H_9$ cells in 1 ml medium containing $1.89\times10^{-2}$ picogram T24 viral antigen per cell, and either 0, 10, 25, or 50 $\mu$g of CRL-8133, are incubated at 37° C. in 5% $CO_2$ for one hour. After this time, the cells are pelleted at 3,000 rpm and washed to remove access non-adsorbed virus. The cells are plated in medium in dishes containing wells of 1 cm diameter. The cultures and the controls, all done in triplicate, are incubated at 37° C., 5% $CO_2$, and the volume in each well is maintained at a constant volume of 1 ml. The media contains either 10, 25, or 50 $\mu$g per ml of CRL-8133. Virus yields in terms of total picogram of T24HIV antigen and cell counts are determined on day seven of the incubation period. Cell viability is determined by trypan blue exclusion.

As can be seen in FIG. 12, there is at least a one and one/half log reduction in virus yield evident at the low concentration of 10 $\mu$g per ml of CRL-8133. Furthermore, the higher concentrations of CRL-8133 did not appear to mediate further reductions in viral replication.

According to these results, the CRL-8133 copolymer is considered an effective inhibitor of HIV application in $H_9$ cells.

EXAMPLE V

Compounds

Samples of AZT was synthesized and purified by a modification of the method of Lin and Prusoff (Lin, T. -S, and W. H. Prusoff. 1978. Synthesis and biological activity of several amino analogs of thymidine. *J. Med. Chem.* 21:109–112).

Antiviral studies

Cells: Human peripheral blood mononuclear cells (PBMC) from healthy IIV-1 seronegative and hepatitis B virus sero-negative donors were isolated by Ficoll-Hypaque discontinuous gradient centrifugation at 1,000×g for 30 minutes, washed twice in phosphate-buffered saline (pH 7.2; PBS), and pelleted at 300×g for 10 minutes. Before infection, the cells were stimulated by phytohemagglutinin (PHA) at a concentration of 16.7 $\mu$g/ml for three days in RPMI 1640 medium supplemented with 15% heat-inactivated fetal calf serum, 1.5 mM L-glutamine, penicillin (100 U/ml), streptomycin (100 $\mu$g/ml), and 4 mM sodium bicarbonate buffer.

Viruses

HIV-1 (strain LAV-1) was obtained from Dr. P. Feorino (Centers for Disease Control, Atlanta, Ga.). The virus was propagated in human PBMC using RPMI 1640 medium, as described previously (McDougal, J. S., S. P. Cort, M. S. Kennedy, C. D. Cabridilla, P. M. Feorino, D. P. Francis, D. Hicks, V. S. Kalyanaramen, and L. S. Martin. 1985. Immunoassay for the detection and quantitation of infectious human retrovirus, lymphadenopathy-associated virus (LAV). J. Immun. Meth. 76:171–183) without PHA or fungizone and supplemented with 7% v/v interleukin-2 (Advanced Biotechnologies, Silver Spring, Md.), 7 $\mu$g/ml DEAE-dextran (Pharmacia, Uppsala, Sweden), and 370 U/ml anti-human leukocyte (alpha) interferon (ICN, Lisle, Ill.). Virus obtained from cell-free culture supernatant was titrated and stored in aliquots at −70° C. until use.

Inhibition of virus replication in human PBMC

Uninfected PHA-stimulated human PBMC were uniformly distributed among 25 $cm^2$ flasks to give a 5 ml suspension containing about $2\times10^6$ cells/ml. Suitable dilutions of virus were added to infect the cultures. The mean reverse transcriptase (RT) activity of the inocula was 50,000 dpm/ml corresponding to about 100 $TCID_{50}$, as determined by Groopman et al. (Groopman J. E., P. M. Benz, R. Ferriani, K. Mayer, J. D. Allan, and L. A. Weymouth. 1987. Characterization of serum neutralization response to the human immunodeficiency virus (HIV). AIDS Res. Human Retro. 3:71–85). The drugs at twice their final concentrations in 5 ml of RPMI 1640 medium, supplemented as described above, were added to the cultures. Uninfected and untreated PBMC at equivalent cell densities were grown in parallel as controls. The cultures were maintained in a humidified 5% $CO_2$-95% air incubator at 37° C. for six days after infection at which point all cultures were sampled for supernatant RT activity. Previous studies had indicated that maximum RT levels were obtained at that time.

Reverse Transcriptase (RT) activity assay

Six ml supernatant from each culture was clarified from cells at 300×g for 10 minutes. Virus particles were pelleted from 5 ml samples at 40,000 rpm for 30 minutes using a Beckman 70.1 Ti rotor and suspended in 200 $\mu$l of virus disrupting buffer (50 mM Tris-HCl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira et al. (Spira, T. J., L. H. Bozeman, R. C. Holman, D. T. Warfield, S. K. Phillips, and P. M. Feorino. 1987. Micromethod for assaying the reverse transcriptase of LAV-HTLV-III/lymphadenopathy-associated virus. J. Clin. Microbiol. 25:97–99). The reaction mixture, which contained 50 mM Tris-HCl pH 7.8, 9 mM $MgCl_2$, 5 mM dithiothreitol, 4.7 $\mu$g/ml $(rA)_n\cdot(dT)_{12-18}$, 140 $\mu$M dATP, and 0.22 $\mu$M $[^3H]$TTP (specific activity 78.0 Ci/mmol, equivalent to 17,300 cpm/pmol; NEN Research Products, Boston, Mass.), was added to each well. The sample (20 $\mu$l) was added to the reaction mixture which was then incubated at 37° C. for 2 hours. The reaction was terminated by the addition of 100 $\mu$l 10% trichloroacetic acid (TCA) containing 0.45 mM sodium pyrophosphate. The acid-insoluble nucleic acids which precipitated were collected on glass filters using a Skatron semi-automatic harvester (setting 9). The filters were washed with 5% TCA and 70% ethanol, dried, and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (Model 2,000CA). The results were expressed in dpm/ml of original clarified supernatant. The procedures for the anti-HIV-1 assays in PBMC described above have been published recently (see Schinazi, R. F. et al in *Antimicrob. Agents Chemother.* 32:1784–1789, December 1988).

Cytotoxicity studies

Toxicity in Vero (African Green Monkey) cells. Vero cells in growth medium (2.5 ml) were added to 25 cm² flasks (Falcon) in duplicate at a concentration equivalent to one tenth of cell confluency for each compound under test. After incubation at 37° C. in a 5% $CO_2$-95% air for 24 hr, the test compound (2×final concentration), dissolved in 2.5 ml of the growth medium was added, and two flasks were harvested immediately by decanting the medium, washing once with 3 ml of PBS, and then incubating at 37° C. for 5 minutes with 3 ml of trypsin/EDTA (0.125%/0.02%). The cells dislodged from the flask by the latter procedure are generally in clumps and are dispersed by repeated forceful pipetting of the suspension against the surface of the flask. To 1 ml of the well-dispersed cell suspension, 0.2 ml of trypan blue solution was added, and the number of cells were counted using a hemacytometer. Each day for the next 3 days, two of the remaining flasks were harvested in the manner just described for determination of cell number. (This method has previously been described—see Schinazi, R. F., Peters, J., Williams, C. C., Chance, D., and Nahmias, A. J.: Effect of combination of acyclovir, and vidarabine or its 5'-monophosphate on herpes simplex viruses in cell culture and in mice. *Antimicrob. Agents Chemother.* 22:499–507, 1982).

PBM proliferation assay.

The drugs were evaluated for their potential toxic effects on uninfected PHA-stimulated human PBM cells and also in CEM cells. The cells were cultured with and without drug for 6 days at which time aliquots were counted for cell viability as described above. Results are shown in Table III.

Median-effect method $EC_{50}$ and $IC_{50}$ values were obtained by analysis of the data using the median-effect equation (Chou, T. -C., and P. Talalay. 1984. Quantitative analysis of dose-effect relationships: the combined effects of multiple drugs or enzyme inhibitors. *Adv. Enz. Regul.* 22:27–55). Results are shown in Tables III and IV.

TABLE III

Effect of AZT and copolymers on the growth of uninfected mitogen stimulated human peripheral blood mononuclear cells (PBMC) and Vero cells.

| Treatment | Concn. ($\mu$M) | % Growth inhibition | |
|---|---|---|---|
| | | PBMC[a] | Vero[b] |
| AZT | 0.1 | −8.9 | −1.8 |
| | 1 | −2.2 | 10.2 |
| | 10 | 5.5 | 20.7 |
| | 50 | 16.8 | 47.4 |
| | 100 | 28.4 | 66.3 |
| CRL-8133 | 1 | −5.1 | 13.7 |
| | 10- | 7.3 | 45.3 |
| | 100 | 82.2 | 77.5 |
| | 200 | 88.2 | 87.4 |
| CRL-85221 | 1 | −5.1 | −13.7 |
| | 10 | 65.1 | 27.7 |
| | 100 | 72.2 | 100 |

TABLE III-continued

Effect of AZT and copolymers on the growth of uninfected mitogen stimulated human peripheral blood mononuclear cells (PBMC) and Vero cells.

| Treatment | Concn. ($\mu$M) | % Growth inhibition | |
|---|---|---|---|
| | | PBMC[a] | Vero[b] |
| | 200 | 88.7 | 100 |
| CRL-8143 | 1 | 1.8 | 29.8 |
| | 10 | −8.9 | 31.2 |
| | 100 | 56.4 | 48.1 |
| | 200 | 73.6 | 48.8 |
| CRL-8141 | 1 | 8.3 | −29.1 |
| | 10 | −12.4 | 6.0 |
| | 100 | 78.9 | 59.3 |
| | 200 | 83.3 | 65.6 |
| CRL-8131 | 1 | −2.8 | 15.1 |
| | 10 | 16.4 | 17.9 |
| | 100 | 83.5 | 80.4 |
| | 200 | 86.6 | 94.4 |

[a]PBMC were counted after drug exposure for 6 days by the trypan blue exclusion method. Untreated cultures had $4.93 \times 10^5$ cells/ml.
[b]Vero cells were counted after drug exposure for 4 days. Untreated cultures had $3.56 \times 10^5$ cells/ml.

TABLE IV

Summary of antiviral and cytotoxicity studies

| Treatment | Anti-HIV-1 in PBMC: $EC_{50}$ ($\mu$M) | Cytotoxicity: $EC_{50}$ ($\mu$M) | |
|---|---|---|---|
| | | PBMC | Vero |
| AZT | 0.0056 | >100 | 50.6 |
| CRL-8133 | 5.13 | 65.9 | 14.8 |
| CRL-85221 | 4.34 | 35.9 | 10.8 |
| CRL-8143 | 6.43 | 93.3 | >200 |
| CRL-8141 | 1.53 | 21.7 | 64.0 |
| CRL-8131 | 2.54 | 34.7 | 33.1 |

EXAMPLE VI

Copolymers CRL-8131, CRL-8141, L103 and L123 were solubilized at 400 $\mu$g/ml in ice cold phosphate buffered saline. The cold solutions were filter sterilized on 0.22 $\mu$m filters and stored at 4° C. Each of the four compounds became soluble under these conditions.

The effects of the copolymers on macrophage phagocytosis was measured by uptake of *Candida albicans*. Monolayers of BALB/c mouse peritoneal macrophages were treated with the indicated copolymer for 18 hours prior to challenge with heat killed *Candida albicans* at a ratio of 5 yeast cells per macrophage. After one hour, the monolayers were washed to remove extracellular yeasts. The cells were then fixed, stained and the intracellular yeast bodies were counted. These results are summarized in Table V.

TABLE V

| Group (40 $\mu$g/ml) | % macrophages with Candida | No. Candida per macrophage |
|---|---|---|
| CRL-8131 | 41.1 (4.9) | 1.74 (0.18) |
| CRL-8141 | 41.8 (3.4) | 2.06 (0.25) |
| L103 | 31.4 (0.9) | 2.33 (0.16) |
| L123 | 57.3 (6.4) | 2.30 (0.06) |
| Control | 52.0 (2.1) | 2.09 (0.23) |

The pretreatment of macrophages with copolymers was not toxic as defined the ability of the macrophage to phagocytose particles. Giemsa staining indicated that the morphology of the macrophages was not altered.

EXAMPLE VII

Macrophage monolayers were pretreated with the indicated copolymers for 18 hours. The macrophages were then challenged with Toxoplasma gondii at a concentration of two T. gondii organisms per macrophage. After one hour, non-phagocytized organisms were removed by washing and the medium plus the copolymer was replenished. Monolayers were fixed and enumerated at 24 hours after challenge. As a positive control, interferon-g, IFN-g, (murine recombinant at 200 U/ml) was added to macrophage monolayers 18 hours before challenge with Toxoplasma. These macrophages are activated by the IFN-g and readily kill Toxoplasma.

TABLE VI

| Group | Growth of Toxoplasma gondii |
| --- | --- |
| CRL-8131 | + |
| CRL-8141 | + |
| L103 | + |
| L123 | + |
| Control | +++++ |
| IFN-g | +/- |

These results showed that intracellular Toxoplasma not only did not multiply in infected macrophages over a 24 hour period, but were apparently killed and digested by the phagocytes. Although the macrophages were pretreated with the copolymer prior to challenge with the Toxoplasma, it should be noted that during the one hour challenge interval, the macrophages were washed free of the copolymer. Thus, it is unlikely that the copolymer had a direct effect on the parasites while they were extracellular.

EXAMPLE VIII

The experimental protocol is as follows: Cultured human macrophages were infected with M. avium and incubated for 7 days with and without the indicated compound. Samples of the macrophages cultures were taken at 0, 4, and 7 days after infection. The macrophages of the samples were lysed, the lysates diluted, and diluted samples of the lysates cultured on 7H10 agar plates to count viable bacteria (CFU).

The bacteria multiply progressively in unprotected macrophages. Inhibition by drugs is evident by retarded or arrested intra-macrophages bacterial multiplication, or by diminished CFU with time indicating death of intra-macrophages bacteria. In this model, there is no significant extracellular multiplication of the M. avium. Any inhibition of bacteria as measured by effects on CFU counts, thus indicated inhibition of intracellular bacteria.

Two serovars most often found associated with AIDS, and originally isolated from AIDS patients, were used. Serovar 4 strain 7497 was purposely used in mixture of phenotypes smooth-transparent (ST) and round-domed (RD). ST is the virulent phenotype and multiplies progressively in macrophages; RD usually do not multiply and may be killed by the macrophages and thus are the avirulent phenotype. Serovar 8 strain T-138 was a highly virulent, pure, ST phenotype.

Each experiment had a negative control group without drug. Other groups had copolymers added once, immediately after infection, usually at three different concentrations ($10^4$, $10^{-5}$ and $10^{-6}$M). Each experiment also had an Ana-samycin ("LSM") positive control at 1 ug/ml to demonstrate effective suppression of the M. avium within macrophages, and combinations of LSM and the copolymers were used to look for synergy between the two. Certain experiments had variations of these groups, or other groups. Macrophages used in these experiments were obtained from healthy volunteers.

Figure 13:
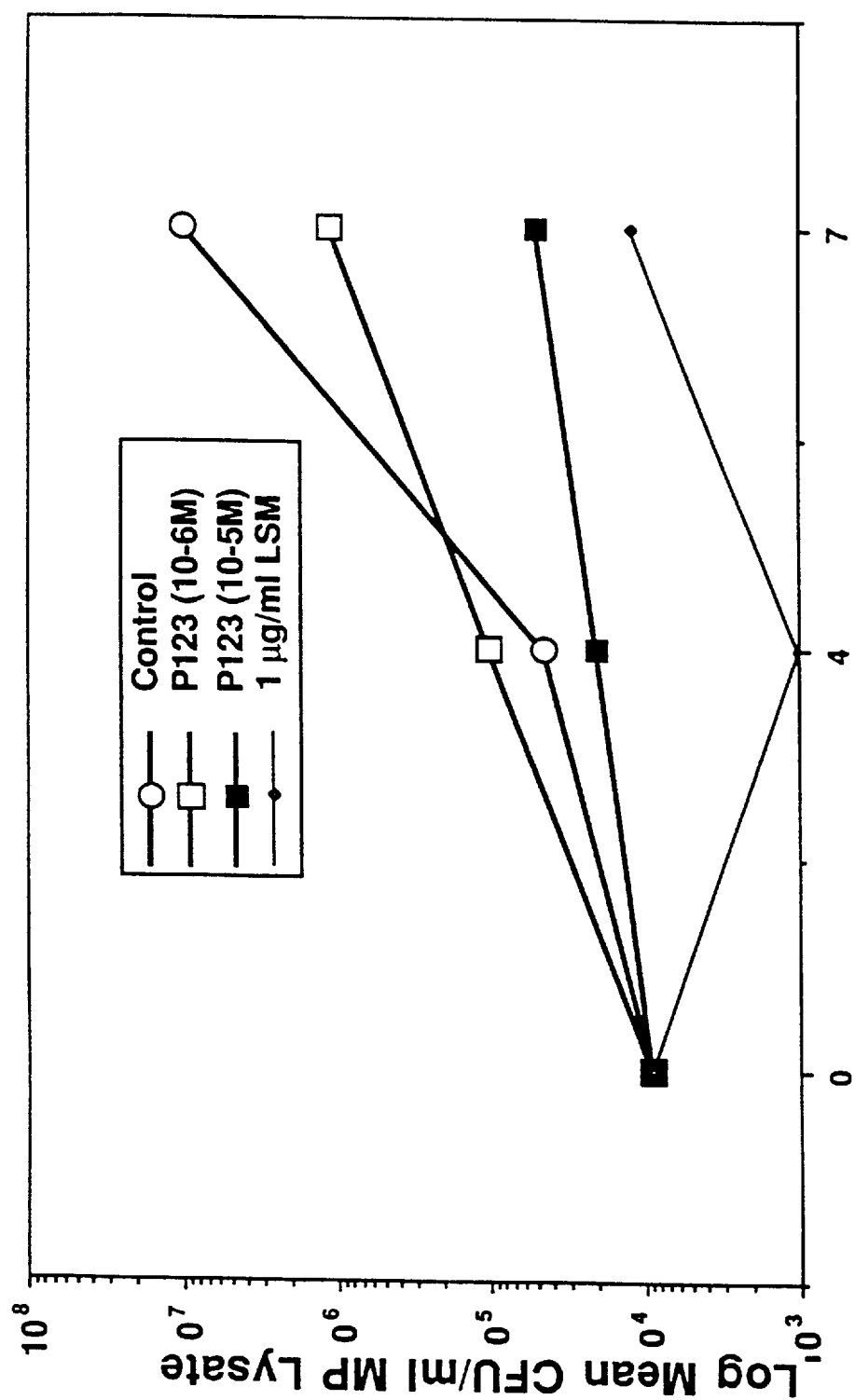
FIG. 13 is a graphical representation of the effect of CRL-8143 copolymer on the viability of intracellular *Mycobacterium avium*.

As shown in FIG. 13, the copolymer CRL-8143 significantly inhibited the growth of mycobacteria designated T-138 at a dose of $1 \times 10^{-5}$M.

EXAMPLE IX

Experiments were conducted to examine the combination of CRL-8131 and CRL-8142 with pyrimethamine, sulfadiazine or clindamycin for in vivo activity against Toxoplasma gondii. CRL-8131 was combined with two percent Tween 80 and 1 percent ethanol, and CRL-8142 was combined with one percent Tween 80 and 5 percent ethanol. A series of experiments were conducted with mice infected either by intraperitoneal (IP) injection of tachyzoites of the R.H. strain or orally with cysts of $C_{56}$ strain.

Methods

Intraperitoneal Infection

Mice were Swiss-Webster females weighing 20 grams at the beginning of the experiment. Infection was IP with $10^3$ tachyzoites. Treatment with CRL-8131 or CRL-8142 alone was administered intraperitoneally. Doses of 25 (CRL-8131) or 25 or 50 (CRL-8142) mg/kg/day were used. When these compounds were used in combination with pyrimethamine, sulfadiazine or clindamycin they were administered IP and the antibiotic was administered orally by gavage or in the drinking water. Pyrimethamine was used at 10 mg/kg/day, sulfadiazine at 80 mg/L drinking water and clindamycin at 150 mg/kg/day.

Treatment was initiated 24 hours after infection and continued for 10 days. Mice dying during treatment and after its discontinuation were examined for presence of T. gondii tachyzoites in intraperitoneal fluid.

Oral infection

Mice were as above and an infection was with 10 cysts of the $C_{56}$ strain of T. gondii administered orally by gavage. Treatment with the copolymers alone was administered IP at the doses described above. When combinations were used the copolymers was administered IP and the other drugs, at the concentrations described above, orally by gavage or in the drinking water. Treatment was initiated three days after infection and continued for ten days. Mice were examined for presence of T. gondii as above.

Results

Figure 18:
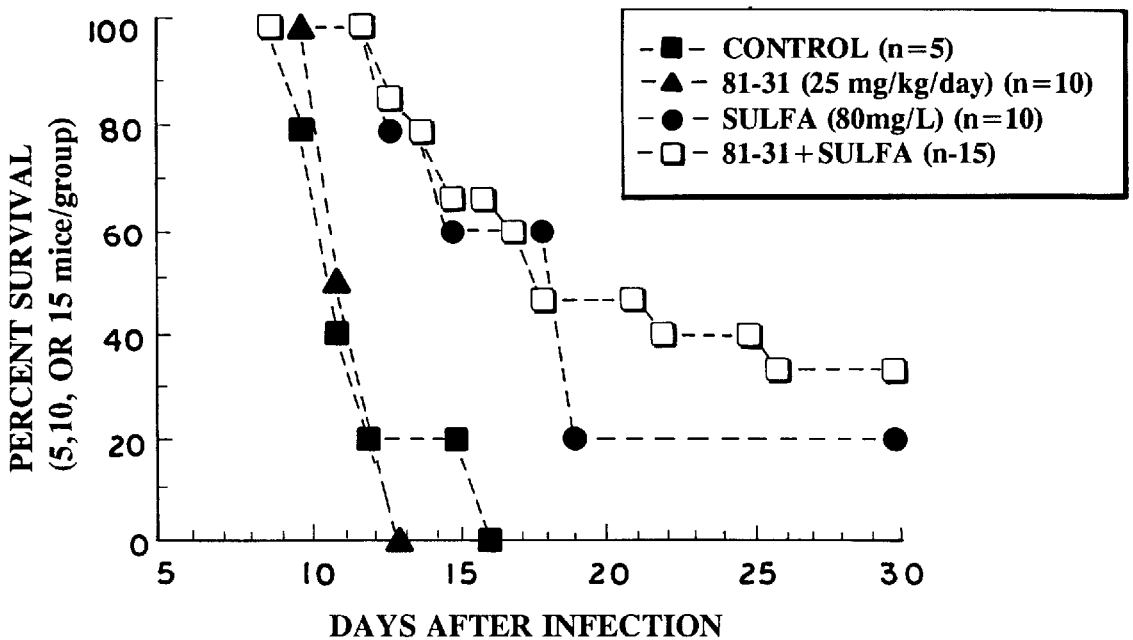
FIG. 18 is a graphical representation of the activity of CRL-8131 plus sulfadiazine in mice infected orally with cysts of the $C_{56}$ strain of *T. gondii*.
Figure 19:
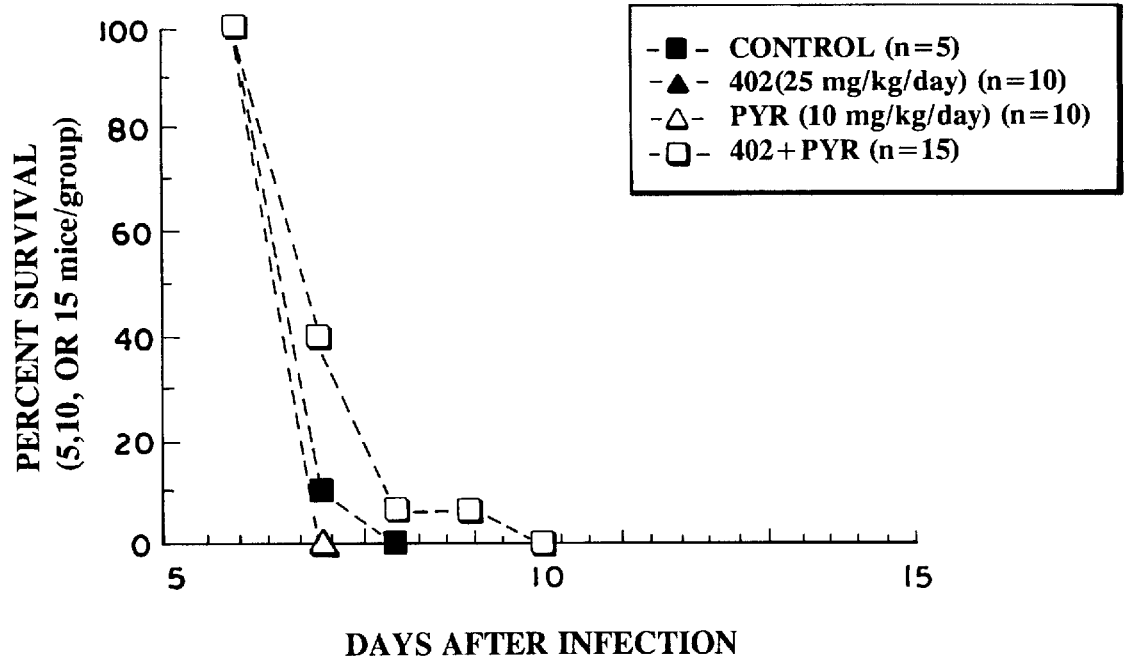
FIG. 19 is a graphical representation of the activity of CRL-8142 plus pyrimethamine in mice infected intraperitoneally with tachyzoites of strain RH of *T. gondii*.
Figure 20:
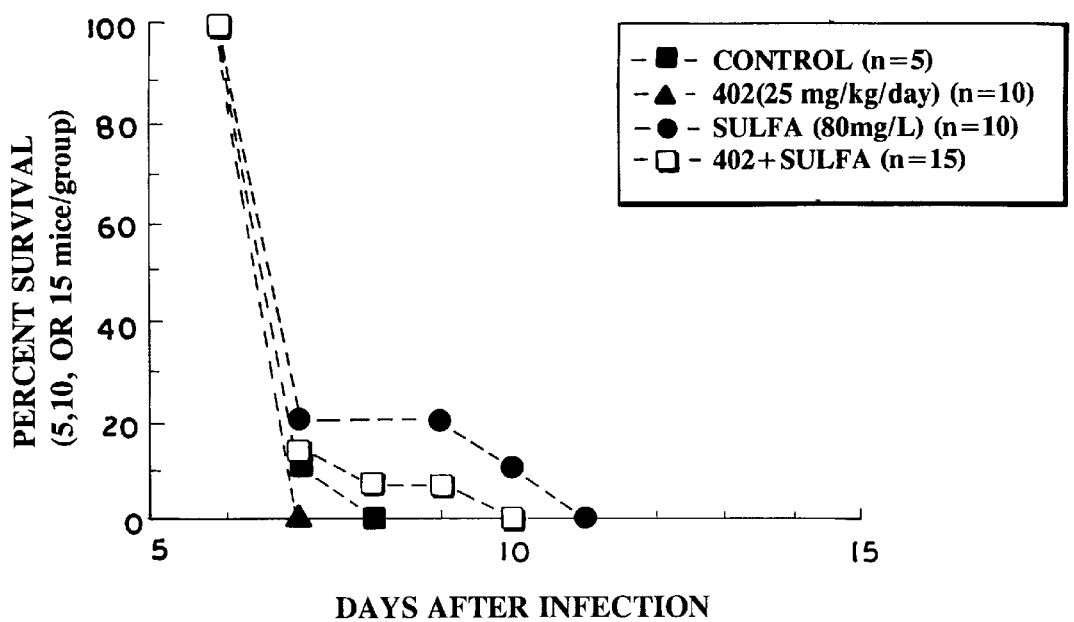
FIG. 20 is a graphical representation of the activity of CRL-8142 plus sulfadiazine in mice infected intraperitoneally with tachyzoites of strain RH of *T. gondii*.
Figure 21:
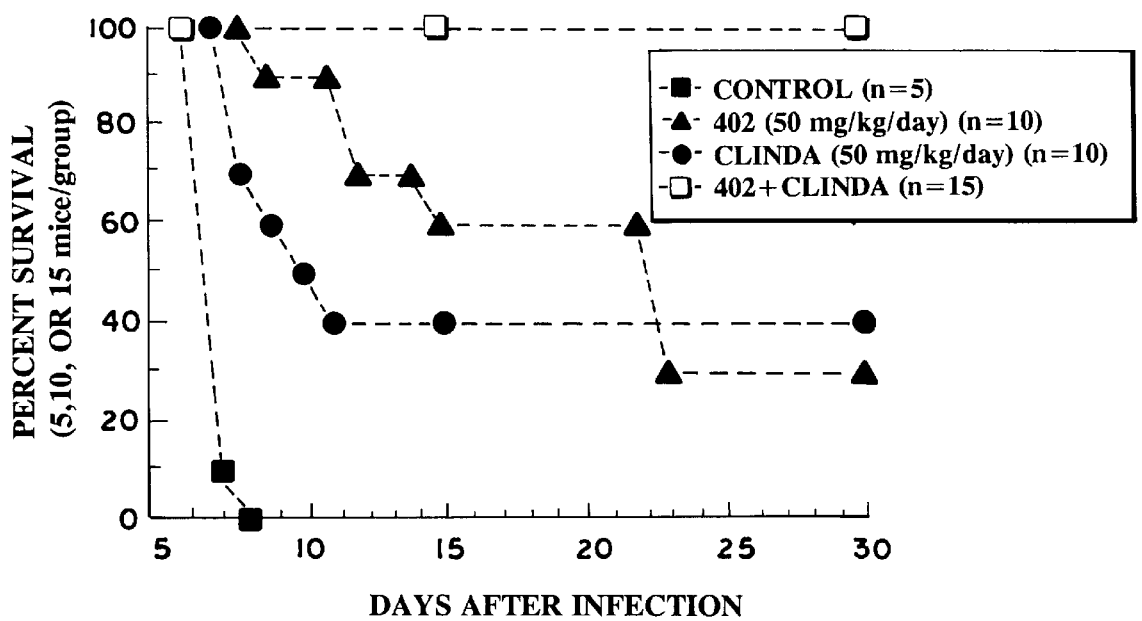
FIG. 21 is a graphical representation of the activity of CRL-8142 plus clindamycin in mice infected intraperitoneally with tachyzoites of strain RH of *T. gondii*.

Survival in mice infected intraperitoneally with tachyzoites of the RH strain of T. gondii was considerably increased following treatment when 25 mg/kg/day of CRL-8131 in combination with each one of the other drugs (FIGS. 14–16). However, in mice infected orally with tissue cysts there was no significant increase in survival (FIGS. 17 and 18). CRL-8142 was not as effective in mice infected intraperitoneally with RH T. gondii when used at the same dose as CRL-8131 (FIGS. 19 and 20). However, significant prolongation in time to death was noted when the concentration of CRL-8142 was increased to 50 mg/kg/day (FIG. 21). Unexpectedly, the combination of this concentration of CRL-8142 with clindamycin resulted in 100 percent survival of infected mice (FIG. 21).

Figure 22:
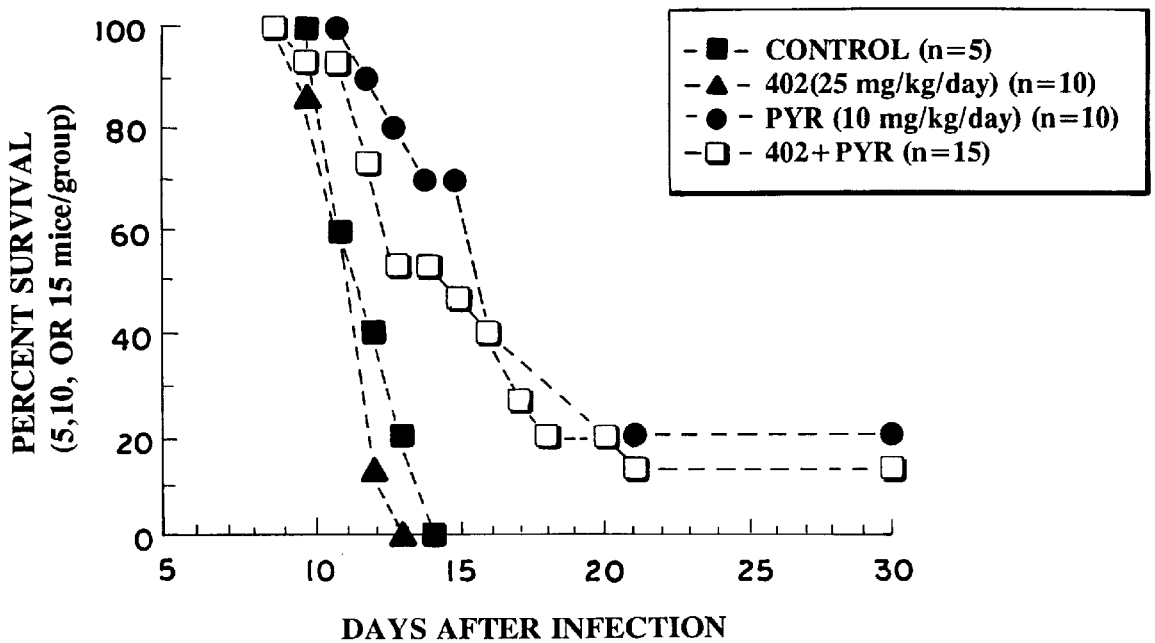
FIG. 22 is a graphical representation of the activity of CRL-8142 plus pyrimethamine in mice infected orally with cysts of the $C_{56}$ strain of *T. gondii*.
Figure 23:
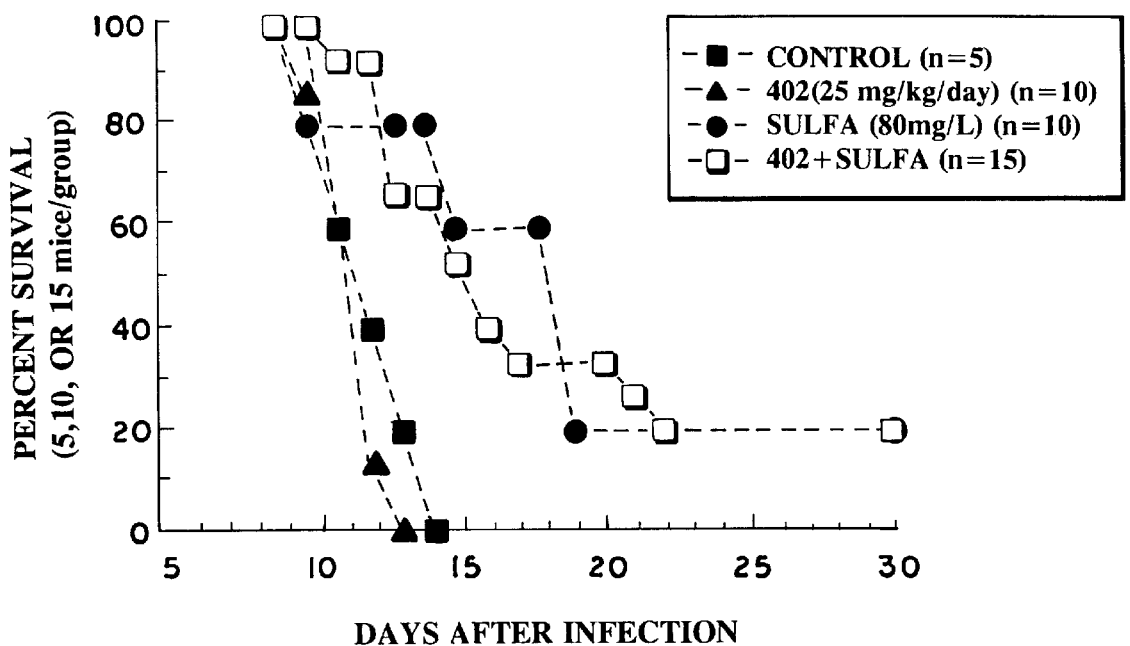
FIG. 23 is a graphical representation of the activity of CRL-8142 plus sulfadiazine in mice infected orally with cysts of the $C_{56}$ strain of *T. gondii*.

Combination of a dose of 25 mg/kg/day of CRL-8142 with each one of the other drugs did not reveal any activity against oral infection with cysts of $C_{56}$ strain of T. gondii (FIGS. 22 and 23).

EXAMPLE X

Figure 24:
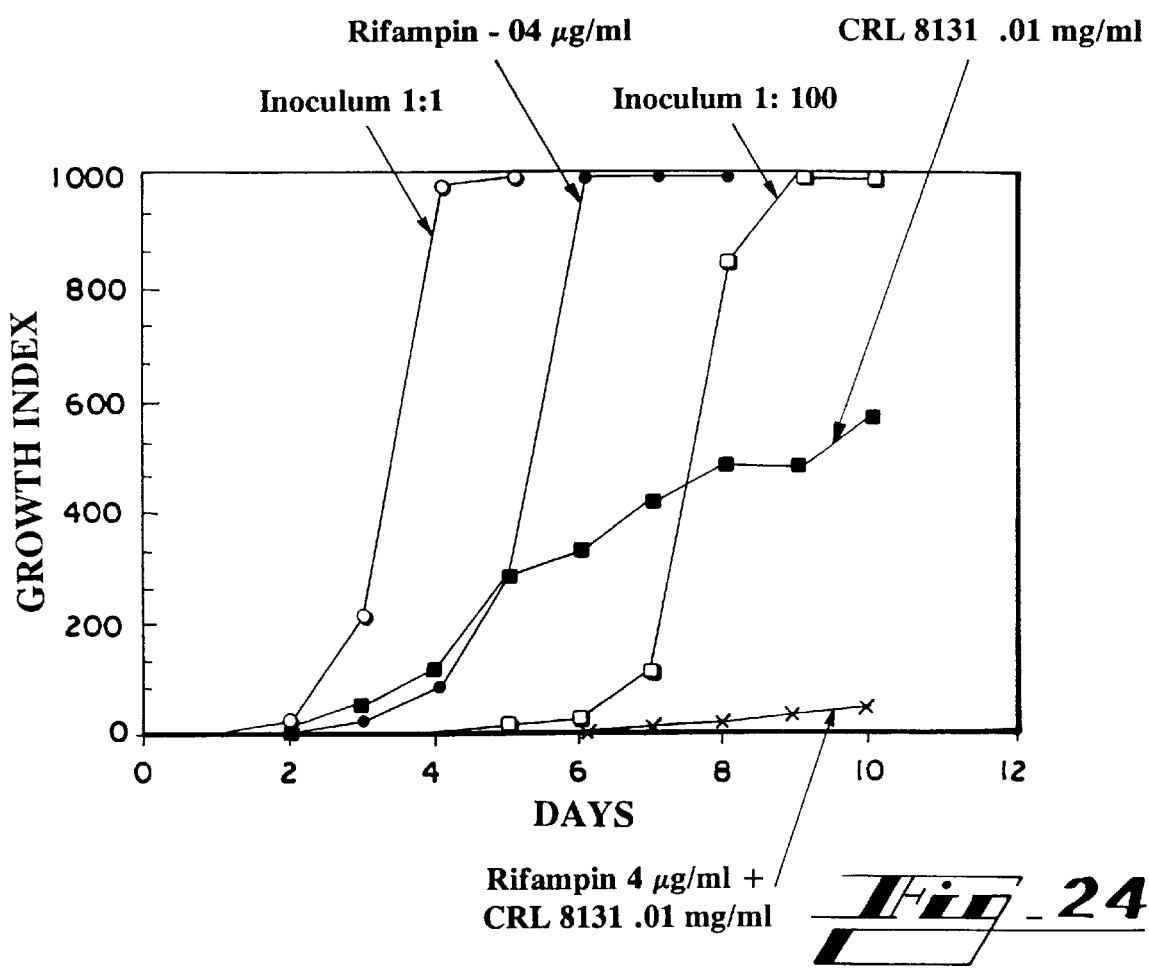
FIG. 24 is a graphic illustration of the synergistic effect of poloxamer formulation CRL-8131 in combination with rifampin.

Growth studies as described above in Example 1 were conducted to study the effect of rifampin alone, CRL-8131 alone, and a combination of rifampin and CRL-8131. Rifampin at a concentration of 0.04 ug/ml was effective in inhibiting growth of *M. avium* as was CRL-8131 at a concentration of 0.01 mg/ml. The combination of rifampin and CRL-8131 at these concentrations, however, unexpectedly and dramatically inhibited growth, and provided almost 100% protection. Results are shown in FIG. 24.

EXAMPLE XI

A therapeutic delivery vehicle is prepared by combining any of the antiinfective copolymers, such as CRL-8131 with any of a variety of antimicrobial agents, such as streptomycin. For CRL-8131 a concentration of three to five percent weight per volume is desirable to construct the therapeutic vehicle. For more hydrophilic copolymer a five to ten percent weight per volume.

300 milligrams of CRL-8131 was added to 10 ml of 0.9% NaCl and the mixture is solubilized by storage at temperatures of 2°–4° C. until a clear solution is formed. 3.0 grams of streptomycin is added to the clear poloxamer solution and mixed thoroughly until the streptomycin is in solution. The final concentration of streptomycin and copolymer in the mixture is 30% weight per volume and 3% weight per volume, respectively.

Micelles associating the copolymer and streptomycin are formed by raising the temperature above 5° C. and allowing the suspension of micelles to equilibrate. The equilibrated suspension is suitable for administration.

It should be understood that the foregoing relates only to preferred embodiments of the present invention and that numerous modifications and alterations may be made without departing from the spirit and scope of the invention as set forth in the appended claims.

We claim:

1. A method of treating an infection in a human or animal caused by a bacteria comprising the step of:

administering an effective amount of a composition nonionic block copolymer into the human or animal, wherein the copolymer has the following general formula:

$$HO(C_2H_4O)_b(C_3H_6O)_a(C_2H_4O)_bH$$

wherein:
 i. the molecular weight represented by the polyoxypropylene portion of the copolymer is between approximately 1,200 and approximately 15,000; and
 ii. the molecular weight represented by the polyoxyethylene portion of the copolymer constitutes between approximately 1% and approximately 50% of the copolymer.

2. The method of claim 1 wherein a is an integer such that the polyoxypropylene portion represented by ($C_3H_6O$) has a molecular weight of about 2,250 to 6,000 and b is an integer such that the polyoxyethylene portion represented by ($C_2H_4O$) constitutes between approximately 5% to 30% by weight of the copolymer.

3. The method of claim 1 wherein a is an integer such that the polyoxypropylene portion represented by ($C_3H_6O$) has a molecular weight of about 2,250 to 4,000 and b is an integer such that the polyoxyethylene portion represented by ($C_2H_4O$) constitutes between approximately 10% to 20% by weight of the copolymer.

4. The method of claim 1 wherein a is an integer such that the polyoxypropylene portion represented by ($C_3H_6O$) has a molecular weight of about 1,200 to 5,300 and b is an integer such that the polyoxyethylene portion represented by ($C_9H_4O$) constitutes between approximately 10% to 50% by weight of the copolymer.

5. The method of claim 1 wherein a is an integer such that the polyoxypropylene portion represented by ($C_3H_6O$) has a molecular weight of about 1,750 to 4,500 and b is an integer such that the polyoxyethylene portion represented by ($C_2H_4O$) constitutes between approximately 10% to 50% by weight of the copolymer.

6. The method of claim 1, wherein the administration of the copolymer is by injection, topical, transdermal, inhalation, trans-mucosal, oral ingestion, and a combination of a plurality of modes of administration.

7. The method of claim 1 wherein the composition further comprises approximately 0.1% to approximately 5% by weight of a surfactant, and approximately 0.5% to approximately 5% by volume of an low molecular weight alcohol.

8. The method of claim 7 wherein the surfactant is polyoxyethylene sorbitan monooleate and the alcohol is ethanol.

9. A composition for treating a human or animal comprising a therapeutic drug admixed with a nonionic block copolymer, wherein the block copolymer has the following formula:

$$HO(C_2H_4O)_b(C_3H_6O)_a(C_2H_4O)_bH$$

wherein:
 i. a is an integer such that the polyoxypropylene portion represented by ($C_3H_6O$) has a molecular weight of between approximately 1,200 and approximately 15,000; and and
 ii. b is an integer such that the molecular weight represented by the polyoxyethylene portion represented by ($C_2H_4O$) constitutes between approximately 1% to 50% by weight of the copolymer.

10. The composition of claim 9 wherein a is an integer such that the polyoxypropylene portion represented by ($C_3H_6O$) has a molecular weight of about 2,250 to 6,000 and b is an integer such that the polyoxyethylene portion represented by ($C_2H_4O$) constitutes between approximately 5% to 30% by weight of the copolymer.

11. The composition of claim 9 wherein a is an integer such that the polyoxypropylene portion represented by ($C_3H_6O$) has a molecular weight of about 2,250 to 4,000 and b is an integer such that the polyoxyethylene portion represented by ($C_2H_4O$) constitutes between approximately 10% to 20% by weight of the copolymer.

12. The composition of claim 9 wherein a is an integer such that the polyoxypropylene portion represented by ($C_3H_6O$) has a molecular weight of about 1,200 to 5,300 and b is an integer such that the polyoxyethylene portion represented by ($C_2H_4O$) constitutes between approximately 10% to 50% by weight of the copolymer.

13. The composition of claim 9 wherein a is an integer such that the polyoxypropylene portion represented by ($C_3H_6O$) has a molecular weight of about 1,750 to 4,500 and b is an integer such that the polyoxyethylene portion represented by ($C_2H_4O$) constitutes between approximately 10% to 50% by weight of the copolymer.

14. The composition of claim 9 wherein the therapeutic drug is selected from the group consisting of rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, AZT, DDI, DDC, and other antiviral nucleoside analogs, foscornat, ganciclovir, viral protease inhibitors, antisense and other modified oligonucleotides, and ribavirin.

15. The composition of claim 9 wherein the therapeutic drug comprises a mixture of several antibiotics.

16. The composition of claim 9 further comprising approximately 0.1% to approximately 5% by weight of a surfactant, and approximately 0.5% to approximately 5% by volume of an low molecular weight alcohol.

17. The composition of claim 16 wherein the surfactant is Tween 80 and the alcohol is ethanol.

18. A method of treating a human or animal comprising administering to a human or animal infected with a bacteria a therapeutic drug and a nonionic block copolymer, wherein the block copolymer has the following formula:

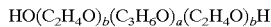

$$HO(C_2H_4O)_b(C_3H_6O)_a(C_2H_4O)_bH$$

wherein:
i. the molecular weight represented by the polyoxypropylene portion of the copolymer is between approximately 1,200 and 15,000; and
ii. the molecular weight represented by the polyoxyethylene portion of the copolymer constitutes between approximately 1% and 50% of the copolymer.

19. The method of claim 18 wherein a is an integer such that the polyoxypropylene portion represented by $(C_3H_6O)$ has a molecular weight of about 2,250 to 6,000 and b is an integer such that the polyoxyethylene portion represented by $(C_2H_4O)$ constitutes between approximately 5% to 30% by weight of the copolymer.

20. The method of claim 18 wherein a is an integer such that the polyoxypropylene portion represented by $(C_3H_6O)$ has a molecular weight of about 2,250 to 4,000 and b is an integer such that the polyoxyethylene portion represented by $(C_2H_4O)$ constitutes between approximately 10% to 20% by weight of the copolymer.

21. The method of claim 18 wherein a is an integer such that the polyoxypropylene portion represented by $(C_3H_6O)$ has a molecular weight of about 1,200 to 5,300 and b is an integer such that the polyoxyethylene portion represented by $(C_2H_4O)$ constitutes between approximately 10% to 50% by weight of the copolymer.

22. The method of claim 18 wherein a is an integer such that the polyoxypropylene portion represented by $(C_3H_6O)$ has a molecular weight of about 1,750 to 4,500 and b is an integer such that the polyoxyethylene portion represented by $(C_2H_4O)$ constitutes between approximately 10% to 50% by weight of the copolymer.

23. The method of claim 18 wherein the administration of the copolymer and the administration of the therapeutic drug are selected from the group consisting of injection, topical, transdermal, inhalation, trans-mucosal, oral ingestion, and a combination of a plurality of modes of administration.

24. The method of claim 18 wherein the nonionic block copolymer is admixed with approximately 0.1% to approximately 5% by weight/volume of a surfactant, and approximately 0.5% to approximately 5% by volume of an low molecular weight alcohol.

25. The method of claim 24 wherein the surfactant is polyoxyethylene sorbitan monooleate and the alcohol is ethanol.

26. The method of claim 18 wherein the therapeutic drug is selected from the group consisting of rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, azidothymidine, dideoxycytidine, dideoxyinosine and other antiviral nucleoside analogs, foscornat, ganciclovir, viral protease inhibitors, antisense and other modified oligonucleotides, and ribavirin.

27. The method of claim 18 wherein the therapeutic drug comprises a mixture of several antibiotics.

28. The method of claim 18 wherein the therapeutic drug is admixed with the copolymer.

29. A method of treating an infection in a human or animal caused by a fungus comprising the step of:
administering an effective amount of a composition nonionic block copolymer into the human or animal, wherein the copolymer has the following general formula:

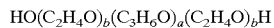

$$HO(C_2H_4O)_b(C_3H_6O)_a(C_2H_4O)_bH$$

wherein:
i. the molecular weight represented by the polyoxypropylene portion of the copolymer is between approximately 1,200 and approximately 15,000; and
ii. the molecular weight represented by the polyoxyethylene portion of the copolymer constitutes between approximately 1% and approximately 50% of the copolymer.

30. The method of claim 29 wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

31. The method of claim 29 wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

32. The method of claim 29 wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

33. The method of claim 29 wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

34. The method of claim 29, wherein the administration of the copolymer is by injection, transdermal, inhalation, trans-mucosal, topical, oral ingestion, and a combination of a plurality of modes of administration.

35. The method of claim 29 wherein the composition further comprises approximately 0.1% to approximately 5% by weight of a surfactant, and approximately 0.5% to approximately 5% by volume of an low molecular weight alcohol.

36. The method of claim 35 wherein the surfactant is polyoxyethylene sorbitan monooleate and the alcohol is ethanol.

37. The method of 29, wherein the fungus is a Candida species.

38. The method of claim 37, wherein the Candida species is *Candida albicans*.

39. A method of treating a human or animal comprising administering to a human or animal infected with a fungus a therapeutic drug and a nonionic block copolymer, wherein the block copolymer has the following formula:

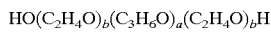

$$HO(C_2H_4O)_b(C_3H_6O)_a(C_2H_4O)_bH$$

wherein:
 i. the molecular weight represented by the polyoxypropylene portion of the copolymer is between approximately 1,200 and 15,000; and
 ii. the molecular weight represented by the polyoxyethylene portion of the copolymer constitutes between approximately 1% and 50% of the copolymer.

40. The method of claim 39 wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

41. The method of claim 39 wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

42. The method of claim 39 wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

43. The method of claim 39 wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

44. The method of claim 39, wherein the administration of the copolymer is by injection, transdermal, inhalation, transmucosal, topical, oral ingestion, and a combination of a plurality of modes of administration.

45. The method of claim 39 wherein the composition further comprises approximately 0.1% to approximately 5% by weight of a surfactant, and approximately 0.5% to approximately 5% by volume of an low molecular weight alcohol.

46. The method of claim 45 wherein the surfactant is polyoxyethylene sorbitan monooleate and the alcohol is ethanol.

47. The method of claim 39, wherein the bacteria is selected from the group consisting of *Mycobacterium tuberculosis, Mycobacterium avium, Mycobacterium leprae, Chlamydia trachomatis, Chlamydia pneumoniae, Chlamydia psittaei,* and *Listeria monocytogenes.*

48. The method of claim 39, wherein the fungus is a Candida species.

49. The method of claim 48, wherein the Candida species is *Candida albicans.*

50. A method of treating an infection in a human or animal caused by a protozoa comprising the step of:
 administering an effective amount of a composition nonionic block copolymer into the human or animal, wherein the copolymer has the following general formula:

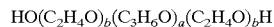

$$HO(C_2H_4O)_b(C_3H_6O)_a(C_2H_4O)_bH$$

wherein:
 i. the molecular weight represented by the polyoxypropylene portion of the copolymer is between approximately 1,200 and approximately 15,000; and
 ii. the molecular weight represented by the polyoxyethylene portion of the copolymer constitutes between approximately 1% and approximately 50% of the copolymer.

51. The method of claim 50 wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

52. The method of claim 50 wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

53. The method of claim 50, wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

54. The method of claim 50, wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

55. The method of claim 50, wherein the administration of the copolymer is by injection, transdermal, inhalation, transmucosal, topical, oral ingestion, and a combination of a plurality of modes of administration.

56. The method of claim 50, wherein the composition further comprises approximately 0.1% to approximately 5% by weight of a surfactant, and approximately 0.5% to approximately 5% by volume of an low molecular weight alcohol.

57. The method of claim 56, wherein the surfactant is polyoxyethylene sorbitan monooleate and the alcohol is ethanol.

58. The method of claim 50, wherein the protozoa is a Toxoplasma species.

59. A method of treating a human or animal comprising administering to a human or animal infected with a protozoa a therapeutic drug and a nonionic block copolymer, wherein the block copolymer has the following formula:

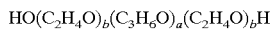

wherein:
i. the molecular weight represented by the polyoxypropylene portion of the copolymer is between approximately 1,200 and 15,000; and
ii. the molecular weight represented by the polyoxyethylene portion of the copolymer constitutes between approximately 1% and 50% of the copolymer.

60. The method of claim 59, wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

61. The method of claim 59, wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

62. The method of claim 59, wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

63. The method of claim 59, wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

64. The method of claim 59, wherein the administration of the copolymer is by injection, transdermal, inhalation, transmucosal, topical, oral ingestion, and a combination of a plurality of modes of administration.

65. The method of claim 59, wherein the composition further comprises approximately 0.1% to approximately 5% by weight of a surfactant, and approximately 0.5% to approximately 5% by volume of an low molecular weight alcohol.

66. The method of claim 65, wherein the surfactant is polyoxyethylene sorbitan monooleate and the alcohol is ethanol.

67. A method of treating an infection in a human or animal caused by a virus comprising the step of:
administering an effective amount of a composition nonionic block copolymer into the human or animal, wherein the copolymer has the following general formula:

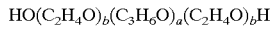

wherein:
i. the molecular weight represented by the polyoxypropylene portion of the copolymer is between approximately 1,200 and approximately 15,000; and
ii. the molecular weight represented by the polyoxyethylene portion of the copolymer constitutes between approximately 1% and approximately 50% of the copolymer.

68. The method of claim 67 wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

69. The method of claim 67, wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

70. The method of claim 67, wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

71. The method of claim 67, wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

72. The method of claim 67, wherein the administration of the copolymer is by injection, transdermal, inhalation, transmucosal, topical, oral ingestion, and a combination of a plurality of modes of administration.

73. The method of claim 67, wherein the composition further comprises approximately 0.1% to approximately 5% by weight of a surfactant, and approximately 0.5% to approximately 5% by volume of an low molecular weight alcohol.

74. The method of claim 73, wherein the surfactant is polyoxyethylene sorbitan monooleate and the alcohol is ethanol.

75. A method of treating a human or animal comprising administering to a human or animal infected with a virus a therapeutic drug and a nonionic block copolymer, wherein the block copolymer has the following formula:

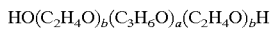

wherein:
i. the molecular weight represented by the polyoxypropylene portion of the copolymer is between approximately 1,200 and 15,000; and
ii. the molecular weight represented by the polyoxyethylene portion of the copolymer constitutes between approximately 1% and 50% of the copolymer.

76. The method of claim 75, wherein the molecular weight represented by the polyoxypropylene portion of the copolymer is between approximately 2250 and approximately 6000, and the molecular weight represented by the polyoxyethylene portion of the copolymer constitutes between approximately 5% and approximately 30% of the copolymer.

77. The method of claim 75, wherein the molecular weight represented by the polyoxypropylene portion of the copolymer is between approximately 2250 and approximately 4000, and the molecular weight represented by the polyoxyethylene portion of the copolymer constitutes between approximately 10% and 20% of the copolymer.

78. The method of claim 75, wherein the molecular weight represented by the polypropylene portion of the copolymer is between approximately 1,200 and 5,300, and the molecular weight represented by the polyoxyethylene portion of the copolymer constitutes between approximately 10% and 50% of the copolymer.

79. The method of claim 75, wherein the molecular weight represented by the polyoxypropylene portion of the copolymer is between approximately 1,750 to 4,500, and the molecular weight represented by the polyoxyethylene portion of the copolymer constitutes between approximately 10% and 50% of the copolymer.

80. The method of claim 75, wherein the administration of the copolymer is by injection, transdermal, inhalation, transmucosal, topical, oral ingestion, and a combination of a plurality of modes of administration.

81. The method of claim 76, wherein the composition further comprises approximately 0.1% to approximately 5% by weight of a surfactant, and approximately 0.5% to approximately 5% by volume of an low molecular weight alcohol.

82. The method of claim 81, wherein the surfactant is polyoxyethylene sorbitan monooleate and the alcohol is ethanol.

83. The method of claim 1 wherein the bacteria is selected from the group consisting of *Mycobacterium tuberculosis, Mycobacterium avium, Mycobacterium leprae, Chlamydia trachomatis, Chlamydia pneumoniae, Chiamydia psittaei* and *Listeria monocytogenes.*

84. The method of 67, wherein the virus is HIV or herpes or antigenically-related strains thereof.

85. The method of claim 59, wherein the protozoa is a Toxoplasma species.

86. The method of claim 75, wherein the virus is HIV or herpes or antigenically-related strains thereof.

* * * * *